(12) United States Patent
Boulard et al.

(10) Patent No.: US 9,809,564 B2
(45) Date of Patent: *Nov. 7, 2017

(54) THERMAL EXTRACTION METHOD AND PRODUCT

(71) Applicant: Pharmatherm Chemicals, Inc., Ottawa, Ontario (CA)

(72) Inventors: David Boulard, Gloucester (CA); Robert G. Graham, Ottawa (CA); Barry A. Freel, Ottawa (CA)

(73) Assignee: Pharmatherm Chemicals, Inc., Ottawa, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/812,711

(22) Filed: Jul. 29, 2015

(65) Prior Publication Data

US 2016/0024037 A1 Jan. 28, 2016

Related U.S. Application Data

(63) Continuation of application No. 12/295,916, filed as application No. PCT/CA2007/000535 on Apr. 2, 2007.

(60) Provisional application No. 60/788,045, filed on Apr. 3, 2006.

(51) Int. Cl.
| | |
|---|---|
| *C07D 305/14* | (2006.01) |
| *A61K 36/00* | (2006.01) |
| *A61K 36/13* | (2006.01) |
| *C10B 49/22* | (2006.01) |
| *C10C 5/00* | (2006.01) |
| *C10B 53/02* | (2006.01) |

(52) U.S. Cl.
CPC ............ *C07D 305/14* (2013.01); *A61K 36/00* (2013.01); *A61K 36/13* (2013.01); *C10B 49/22* (2013.01); *C10B 53/02* (2013.01); *C10C 5/00* (2013.01); *Y02E 50/14* (2013.01)

(58) Field of Classification Search
CPC ....... C07D 305/14; C10B 53/02; C10B 49/22; A61K 36/00; A61K 36/13; C10C 5/00; Y02E 50/14
See application file for complete search history.

(56) References Cited

U.S. PATENT DOCUMENTS

| | | | |
|---|---|---|---|
| 1,252,072 A | 1/1918 | Abbot |
| 2,205,757 A | 6/1940 | Wheat |
| 2,318,555 A | 5/1943 | Ruthruff |
| 2,326,525 A | 8/1943 | Diwoky |
| 2,328,202 A | 8/1943 | Doerner |
| 2,380,098 A | 7/1945 | Doerner |
| 2,492,948 A | 1/1950 | Berger |
| 2,566,353 A | 9/1951 | Mills |
| 2,696,979 A | 12/1954 | Berge |
| 2,884,303 A | 4/1959 | William |
| 3,130,007 A | 4/1964 | Breck |
| 3,309,356 A | 3/1967 | Esterer |
| 3,313,726 A | 4/1967 | Campbell et al. |
| 3,445,549 A | 5/1969 | Hakulin |
| 3,467,502 A | 9/1969 | Davis |
| 3,694,346 A | 9/1972 | Blaser et al. |
| 3,696,022 A | 10/1972 | Hutchings |
| 3,760,870 A | 9/1973 | Guetlhuber |
| 3,776,533 A | 12/1973 | Vlnaty |
| 3,814,176 A | 6/1974 | Seth |
| 3,853,498 A | 12/1974 | Bailie |
| 3,876,533 A | 4/1975 | Myers |
| 3,890,111 A | 6/1975 | Knudsen |
| 3,907,661 A | 9/1975 | Gwyn et al. |
| 3,925,024 A | 12/1975 | Hollingsworth et al. |
| 3,927,996 A | 12/1975 | Knudsen et al. |
| 3,959,420 A | 5/1976 | Geddes et al. |
| 4,003,829 A | 1/1977 | Burger et al. |
| 4,032,305 A | 6/1977 | Squires |
| 4,039,290 A | 8/1977 | Inada et al. |
| 4,052,265 A | 10/1977 | Kemp |
| 4,064,018 A | 12/1977 | Choi |
| 4,064,043 A | 12/1977 | Kollman |
| 4,085,030 A | 4/1978 | Green et al. |
| 4,101,414 A | 7/1978 | Kim et al. |
| 4,102,773 A | 7/1978 | Green et al. |
| 4,103,902 A | 8/1978 | Steiner et al. |
| 4,138,020 A | 2/1979 | Steiner et al. |
| 4,145,274 A | 3/1979 | Green et al. |

(Continued)

FOREIGN PATENT DOCUMENTS

| | | |
|---|---|---|
| BR | 8304158 | 7/1984 |
| BR | 8304794 | 4/1985 |

(Continued)

OTHER PUBLICATIONS

Scott, D. S.,"Fast Pyrolysis of Biomass for Recovery of Specialty Chemicals." Developments in thermochemical biomass conversion. Springer Netherlands, 1997. 523-535.*
Nikolakakis, A.,"Taxus canadensis abundant taxane: conversion to paclitaxel and rearrangements." Bioorganic & medicinal chemistry 8.6 (2000): 1269-1280.*
Cass et al. "Challenges in the Isolation of Taxanes from *Taxus canadensis* by Fast Pyrolysis," *J Analytical and Applied Pyrolysis* 57 (2001) 275-285.
Cragg et al. "The Search for New Pharmaceutical Crops: Drug Discovery and Development at the National Cancer Institute," in Janick, J. and Simon, J.E. (eds) *New Crops*, Wiley, New York (1993) 161-167.

(Continued)

*Primary Examiner* — Matt Mauro
(74) *Attorney, Agent, or Firm* — Jones Day

(57) ABSTRACT

The present invention is related to a thermal extract of a plant material and methods of extraction thereof. The method of producing a thermal extract from a plant starting material by means of a thermal extraction of the starting material wherein the improvement consists in requiring smaller amounts of costly and/or toxic organic solvents for the extraction and partitioning steps.

17 Claims, 3 Drawing Sheets

(56) References Cited

U.S. PATENT DOCUMENTS

| | | |
|---|---|---|
| 4,153,514 A | 5/1979 | Garrett et al. |
| 4,157,245 A | 6/1979 | Mitchell et al. |
| 4,165,717 A | 8/1979 | Reh et al. |
| 4,204,915 A | 5/1980 | Kurata et al. |
| 4,210,492 A | 7/1980 | Roberts |
| 4,219,537 A | 8/1980 | Steiner |
| 4,225,415 A | 9/1980 | Mirza et al. |
| 4,233,119 A | 11/1980 | Meyers et al. |
| 4,245,693 A | 1/1981 | Cheng |
| 4,272,402 A | 6/1981 | Mayes |
| 4,284,616 A | 8/1981 | Solbakken et al. |
| 4,298,453 A | 11/1981 | Schoennagel et al. |
| 4,300,009 A | 11/1981 | Haag et al. |
| 4,301,771 A | 11/1981 | Jukkola et al. |
| 4,306,619 A | 12/1981 | Trojani |
| 4,308,411 A | 12/1981 | Frankiewicz |
| 4,311,670 A | 1/1982 | Nieminen et al. |
| 4,317,703 A | 3/1982 | Bowen et al. |
| 4,321,096 A | 3/1982 | Dobbin |
| 4,324,637 A | 4/1982 | Durai-swamy |
| 4,324,641 A | 4/1982 | Durai-Swamy |
| 4,324,642 A | 4/1982 | Durai-swamy |
| 4,324,644 A | 4/1982 | Durai-swamy |
| 4,325,327 A | 4/1982 | Kantesaria et al. |
| 4,334,893 A | 6/1982 | Lang |
| 4,336,128 A | 6/1982 | Tamm |
| 4,341,598 A | 7/1982 | Green |
| 4,344,770 A | 8/1982 | Capener et al. |
| 4,364,796 A | 12/1982 | Ishii et al. |
| 4,373,994 A | 2/1983 | Lee |
| 4,415,434 A | 11/1983 | Hargreaves et al. |
| 4,422,927 A | 12/1983 | Kowalczyk |
| 4,434,726 A | 3/1984 | Jones |
| 4,443,229 A | 4/1984 | Sageman et al. |
| 4,456,504 A | 6/1984 | Spars et al. |
| 4,482,451 A | 11/1984 | Kemp |
| 4,495,056 A | 1/1985 | Venardos et al. |
| 4,504,379 A | 3/1985 | Stuntz et al. |
| 4,537,571 A | 8/1985 | Buxel et al. |
| 4,548,615 A | 10/1985 | Lonchamp et al. |
| 4,552,203 A | 11/1985 | Chrysostome et al. |
| 4,574,743 A | 3/1986 | Claus |
| 4,584,064 A | 4/1986 | Ciais et al. |
| 4,584,947 A | 4/1986 | Chittick |
| 4,595,567 A | 6/1986 | Hedrick |
| 4,615,870 A | 10/1986 | Armstrong et al. |
| 4,617,693 A | 10/1986 | Meyer et al. |
| 4,645,568 A | 2/1987 | Kurps et al. |
| 4,668,243 A | 5/1987 | Schulz |
| 4,678,860 A | 7/1987 | Kuester |
| 4,684,375 A | 8/1987 | Morin et al. |
| 4,710,357 A | 12/1987 | Cetinkaya et al. |
| 4,714,109 A | 12/1987 | Tsao |
| 4,732,091 A | 3/1988 | Gould |
| 4,796,546 A | 1/1989 | Herstad et al. |
| 4,823,712 A | 4/1989 | Wormer |
| 4,828,581 A | 5/1989 | Feldmann et al. |
| 4,849,091 A | 7/1989 | Cabrera et al. |
| 4,880,473 A | 11/1989 | Scott et al. |
| 4,881,592 A | 11/1989 | Cetinkaya |
| 4,891,459 A | 1/1990 | Knight et al. |
| 4,897,178 A | 1/1990 | Best et al. |
| 4,931,171 A | 6/1990 | Piotter |
| 4,940,007 A | 7/1990 | Hiltunen et al. |
| 4,942,269 A | 7/1990 | Chum et al. |
| 4,968,325 A | 11/1990 | Black et al. |
| 4,983,278 A | 1/1991 | Cha et al. |
| 4,987,178 A | 1/1991 | Shibata et al. |
| 4,988,430 A | 1/1991 | Sechrist et al. |
| 4,992,605 A | 2/1991 | Craig et al. |
| 5,009,770 A | 4/1991 | Miller et al. |
| 5,011,592 A | 4/1991 | Owen et al. |
| 5,018,458 A | 5/1991 | Mcintyre et al. |
| 5,041,209 A | 8/1991 | Cha et al. |
| 5,059,404 A | 10/1991 | Mansour et al. |
| 5,077,252 A | 12/1991 | Owen et al. |
| 5,093,085 A | 3/1992 | Engstrom et al. |
| 5,136,117 A | 8/1992 | Paisley et al. |
| 5,212,129 A | 5/1993 | Lomas |
| 5,225,044 A | 7/1993 | Breu |
| 5,236,688 A | 8/1993 | Watanabe et al. |
| 5,239,946 A | 8/1993 | Garcia-mallol |
| 5,243,922 A | 9/1993 | Rehmat et al. |
| 5,281,727 A | 1/1994 | Carver et al. |
| 5,306,481 A | 4/1994 | Mansour et al. |
| 5,326,919 A | 7/1994 | Paisley et al. |
| 5,343,939 A | 9/1994 | Cetinkaya |
| 5,371,212 A | 12/1994 | Moens |
| 5,376,340 A | 12/1994 | Bayer et al. |
| 5,380,916 A | 1/1995 | Rao |
| 5,395,455 A | 3/1995 | Scott et al. |
| 5,402,548 A | 4/1995 | Adair et al. |
| 5,407,674 A | 4/1995 | Gabetta et al. |
| 5,423,891 A | 6/1995 | Taylor |
| 5,426,807 A | 6/1995 | Grimsley et al. |
| 5,478,736 A | 12/1995 | Nair |
| 5,494,653 A | 2/1996 | Paisley |
| 5,520,722 A | 5/1996 | Hershkowitz et al. |
| 5,536,488 A | 7/1996 | Mansour et al. |
| 5,578,092 A | 11/1996 | Collin |
| 5,584,985 A | 12/1996 | Lomas |
| 5,605,551 A | 2/1997 | Scott et al. |
| 5,637,192 A | 6/1997 | Mansour et al. |
| 5,654,448 A | 8/1997 | Pandey et al. |
| 5,662,050 A | 9/1997 | Angelo et al. |
| 5,686,049 A | 11/1997 | Bonifay et al. |
| 5,703,299 A | 12/1997 | Carleton et al. |
| 5,713,977 A | 2/1998 | Kobayashi |
| 5,725,738 A | 3/1998 | Brioni et al. |
| 5,728,271 A | 3/1998 | Piskorz et al. |
| 5,744,333 A | 4/1998 | Cociancich et al. |
| 5,788,784 A | 8/1998 | Koppenhoefer et al. |
| 5,792,340 A | 8/1998 | Freel et al. |
| 5,853,548 A | 12/1998 | Piskorz et al. |
| 5,879,079 A | 3/1999 | Hohmann et al. |
| 5,879,642 A | 3/1999 | Trimble et al. |
| 5,879,650 A | 3/1999 | Kaul et al. |
| 5,904,838 A | 5/1999 | Kalnes et al. |
| 5,915,311 A | 6/1999 | Muller et al. |
| 5,961,786 A | 10/1999 | Freel et al. |
| 5,969,165 A | 10/1999 | Liu |
| 6,002,025 A | 12/1999 | Page et al. |
| 6,011,187 A | 1/2000 | Horizoe et al. |
| 6,033,555 A | 3/2000 | Chen et al. |
| 6,106,702 A | 8/2000 | Sohn et al. |
| 6,113,862 A | 9/2000 | Jorgensen et al. |
| 6,133,499 A | 10/2000 | Horizoe et al. |
| 6,149,765 A | 11/2000 | Mansour et al. |
| 6,190,542 B1 | 2/2001 | Comolli et al. |
| 6,193,837 B1 | 2/2001 | Agblevor et al. |
| 6,237,541 B1 | 5/2001 | Alliston et al. |
| 6,339,182 B1 | 1/2002 | Munson et al. |
| 6,398,921 B1 | 6/2002 | Moraski |
| 6,452,024 B1 | 9/2002 | Bui-Khac et al. |
| 6,455,015 B1 | 9/2002 | Kilroy |
| 6,485,841 B1 | 11/2002 | Freel et al. |
| 6,497,199 B2 | 12/2002 | Yamada et al. |
| 6,547,957 B1 | 4/2003 | Sudhakar et al. |
| 6,555,649 B2 | 4/2003 | Giroux et al. |
| 6,656,342 B2 | 12/2003 | Smith et al. |
| 6,660,157 B2 | 12/2003 | Que et al. |
| 6,676,828 B1 | 1/2004 | Arreaza et al. |
| 6,680,137 B2 | 1/2004 | Paisley |
| 6,743,746 B1 | 6/2004 | Prilutsky et al. |
| 6,759,562 B2 | 7/2004 | Gartside et al. |
| 6,768,036 B2 | 7/2004 | Lattner et al. |
| 6,776,607 B2 | 8/2004 | Nahas et al. |
| 6,808,390 B1 | 10/2004 | Fung |
| 6,814,940 B1 | 11/2004 | Hiltunen et al. |
| 6,844,420 B1 | 1/2005 | Freel et al. |
| 6,875,341 B1 | 4/2005 | Bunger et al. |
| 6,960,325 B2 | 11/2005 | Kao et al. |
| 6,962,676 B1 | 11/2005 | Hyppaenen |
| 6,988,453 B2 | 1/2006 | Cole et al. |

(56) References Cited

U.S. PATENT DOCUMENTS

| | | |
|---|---|---|
| 7,004,999 B2 | 2/2006 | Johnson et al. |
| 7,022,741 B2 | 4/2006 | Jiang et al. |
| 7,026,262 B1 | 4/2006 | Palmas et al. |
| 7,202,389 B1 | 4/2007 | Brem |
| 7,214,252 B1 | 5/2007 | Krumm et al. |
| 7,226,954 B2 | 6/2007 | Tavasoli et al. |
| 7,240,639 B2 | 7/2007 | Hyppaenen et al. |
| 7,247,233 B1 | 7/2007 | Hedrick et al. |
| 7,262,331 B2 | 8/2007 | van de Beld et al. |
| 7,263,934 B2 | 9/2007 | Copeland et al. |
| 7,285,186 B2 | 10/2007 | Tokarz |
| 7,319,168 B2 | 1/2008 | Sanada |
| 7,473,349 B2 | 1/2009 | Keckler et al. |
| 7,476,774 B2 | 1/2009 | Umansky et al. |
| 7,479,217 B2 | 1/2009 | Pinault et al. |
| 7,491,317 B2 | 2/2009 | Meier et al. |
| 7,563,345 B2 | 7/2009 | Tokarz |
| 7,572,362 B2 | 8/2009 | Freel et al. |
| 7,572,365 B2 | 8/2009 | Freel et al. |
| 7,578,927 B2 | 8/2009 | Marker et al. |
| 7,625,432 B2 | 12/2009 | Gouman et al. |
| 7,811,340 B2 | 10/2010 | Bayle et al. |
| 7,897,124 B2 | 3/2011 | Gunnerman et al. |
| 7,905,990 B2 | 3/2011 | Freel |
| 7,943,014 B2 | 5/2011 | Berruti et al. |
| 7,956,224 B2 | 6/2011 | Elliott et al. |
| 7,960,598 B2 | 6/2011 | Spilker et al. |
| 7,982,075 B2 | 7/2011 | Marker et al. |
| 7,998,315 B2 | 8/2011 | Bridgwater et al. |
| 7,998,455 B2 | 8/2011 | Abbas et al. |
| 7,999,142 B2 | 8/2011 | Kalnes et al. |
| 7,999,143 B2 | 8/2011 | Marker et al. |
| 8,043,391 B2 | 10/2011 | Dinjus et al. |
| 8,057,641 B2 | 11/2011 | Bartek et al. |
| 8,097,090 B2 | 1/2012 | Freel et al. |
| 8,097,216 B2 | 1/2012 | Beech et al. |
| 8,147,766 B2 | 4/2012 | Spilker et al. |
| 8,153,850 B2 | 4/2012 | Hall et al. |
| 8,202,332 B2 | 6/2012 | Agblevor |
| 8,207,385 B2 | 6/2012 | O'Connor et al. |
| 8,217,211 B2 | 7/2012 | Agrawal et al. |
| 8,277,643 B2 | 10/2012 | Huber et al. |
| 8,288,600 B2 | 10/2012 | Bartek et al. |
| 8,304,592 B2 | 11/2012 | Luebke |
| 8,314,275 B2 | 11/2012 | Brandvold |
| 8,329,967 B2 | 12/2012 | Brandvold et al. |
| 8,404,910 B2 | 3/2013 | Kocal et al. |
| 8,499,702 B2 | 8/2013 | Palmas et al. |
| 8,519,203 B2 | 8/2013 | Marinangeli et al. |
| 8,519,205 B2 | 8/2013 | Frey et al. |
| 8,524,087 B2 | 9/2013 | Frey et al. |
| 8,575,408 B2 | 11/2013 | Marker et al. |
| 8,715,490 B2 | 5/2014 | Brandvold et al. |
| 8,726,443 B2 | 5/2014 | Freel et al. |
| 9,044,727 B2 | 6/2015 | Kulprathipanja et al. |
| 9,127,208 B2 * | 9/2015 | Boulard .................. A61K 36/00 |
| 2002/0014033 A1 | 2/2002 | Langer et al. |
| 2002/0100711 A1 | 8/2002 | Freel et al. |
| 2002/0146358 A1 | 10/2002 | Smith et al. |
| 2003/0049854 A1 | 3/2003 | Rhodes |
| 2003/0202912 A1 | 10/2003 | Myohanen et al. |
| 2004/0069682 A1 | 4/2004 | Freel et al. |
| 2004/0182003 A1 | 9/2004 | Bayle et al. |
| 2004/0200204 A1 | 10/2004 | Dries et al. |
| 2005/0167337 A1 | 8/2005 | Bunger et al. |
| 2005/0209328 A1 | 9/2005 | Allgood et al. |
| 2006/0010714 A1 | 1/2006 | Carin et al. |
| 2006/0016723 A1 | 1/2006 | Tang et al. |
| 2006/0070362 A1 | 4/2006 | Dewitz et al. |
| 2006/0074254 A1 | 4/2006 | Zhang et al. |
| 2006/0101665 A1 | 5/2006 | Carin et al. |
| 2006/0163053 A1 | 7/2006 | Ershag |
| 2006/0180060 A1 | 8/2006 | Crafton et al. |
| 2006/0185245 A1 | 8/2006 | Serio et al. |
| 2006/0201024 A1 | 9/2006 | Carin et al. |
| 2006/0254081 A1 | 11/2006 | Carin et al. |
| 2006/0264684 A1 | 11/2006 | Petri et al. |
| 2007/0000809 A1 | 1/2007 | Lin et al. |
| 2007/0010588 A1 | 1/2007 | Pearson |
| 2007/0141222 A1 | 6/2007 | Binder et al. |
| 2007/0205139 A1 | 9/2007 | Kulprathipanja et al. |
| 2007/0272538 A1 | 11/2007 | Satchell |
| 2008/0006519 A1 | 1/2008 | Badger |
| 2008/0006520 A1 | 1/2008 | Badger |
| 2008/0029437 A1 | 2/2008 | Umansky et al. |
| 2008/0035526 A1 | 2/2008 | Hedrick et al. |
| 2008/0035528 A1 | 2/2008 | Marker |
| 2008/0050792 A1 | 2/2008 | Zmierczak et al. |
| 2008/0051619 A1 | 2/2008 | Kulprathipanja et al. |
| 2008/0081006 A1 | 4/2008 | Myers et al. |
| 2008/0086937 A1 | 4/2008 | Hazlebeck et al. |
| 2008/0161615 A1 | 7/2008 | Chapus et al. |
| 2008/0171649 A1 | 7/2008 | Jan et al. |
| 2008/0185112 A1 | 8/2008 | Argyropoulos |
| 2008/0189979 A1 | 8/2008 | Carin et al. |
| 2008/0193345 A1 | 8/2008 | Lott et al. |
| 2008/0194896 A1 | 8/2008 | Brown et al. |
| 2008/0199821 A1 | 8/2008 | Nyberg et al. |
| 2008/0230440 A1 | 9/2008 | Graham et al. |
| 2008/0236043 A1 | 10/2008 | Dinjus et al. |
| 2008/0264771 A1 | 10/2008 | Dam-Johansen et al. |
| 2008/0274017 A1 | 11/2008 | Boykin et al. |
| 2008/0274022 A1 | 11/2008 | Boykin et al. |
| 2008/0282606 A1 | 11/2008 | Plaza et al. |
| 2008/0312476 A1 | 12/2008 | McCall |
| 2008/0318763 A1 | 12/2008 | Anderson |
| 2009/0008292 A1 | 1/2009 | Keusenkothen et al. |
| 2009/0008296 A1 | 1/2009 | Sappok et al. |
| 2009/0077867 A1 | 3/2009 | Marker et al. |
| 2009/0077868 A1 | 3/2009 | Brady et al. |
| 2009/0078557 A1 | 3/2009 | Tokarz |
| 2009/0078611 A1 | 3/2009 | Marker et al. |
| 2009/0082603 A1 | 3/2009 | Kalnes et al. |
| 2009/0082604 A1 | 3/2009 | Agrawal et al. |
| 2009/0084666 A1 | 4/2009 | Agrawal et al. |
| 2009/0090046 A1 | 4/2009 | O'Connor et al. |
| 2009/0090058 A1 | 4/2009 | Dam-Johansen et al. |
| 2009/0113787 A1 | 5/2009 | Elliott et al. |
| 2009/0139851 A1 | 6/2009 | Freel |
| 2009/0165378 A1 | 7/2009 | Agblevor |
| 2009/0183424 A1 | 7/2009 | Gorbell et al. |
| 2009/0188158 A1 | 7/2009 | Morgan |
| 2009/0193709 A1 | 8/2009 | Marker et al. |
| 2009/0208402 A1 | 8/2009 | Rossi |
| 2009/0227823 A1 | 9/2009 | Huber et al. |
| 2009/0242377 A1 | 10/2009 | Honkola et al. |
| 2009/0250376 A1 | 10/2009 | Brandvold et al. |
| 2009/0253947 A1 | 10/2009 | Brandvold et al. |
| 2009/0253948 A1 | 10/2009 | McCall et al. |
| 2009/0255144 A1 | 10/2009 | Gorbell et al. |
| 2009/0259076 A1 | 10/2009 | Simmons et al. |
| 2009/0259082 A1 | 10/2009 | Deluga et al. |
| 2009/0274600 A1 | 11/2009 | Jain et al. |
| 2009/0283442 A1 | 11/2009 | McCall et al. |
| 2009/0287029 A1 | 11/2009 | Anumakonda et al. |
| 2009/0293344 A1 | 12/2009 | O'Brien et al. |
| 2009/0293359 A1 | 12/2009 | Simmons et al. |
| 2009/0294324 A1 | 12/2009 | Brandvold et al. |
| 2009/0301930 A1 | 12/2009 | Brandvold et al. |
| 2009/0308787 A1 | 12/2009 | O'Connor et al. |
| 2009/0318737 A1 | 12/2009 | Luebke |
| 2009/0321311 A1 | 12/2009 | Marker et al. |
| 2010/0043634 A1 | 2/2010 | Shulfer et al. |
| 2010/0083566 A1 | 4/2010 | Frederiksen et al. |
| 2010/0133144 A1 | 6/2010 | Kokayeff et al. |
| 2010/0147743 A1 | 6/2010 | MacArthur et al. |
| 2010/0148122 A1 | 6/2010 | Breton et al. |
| 2010/0151550 A1 | 6/2010 | Nunez et al. |
| 2010/0158767 A1 | 6/2010 | Mehlberg et al. |
| 2010/0162625 A1 | 7/2010 | Mills |
| 2010/0163395 A1 | 7/2010 | Henrich et al. |
| 2010/0222620 A1 | 9/2010 | O'Connor et al. |
| 2010/0266464 A1 | 10/2010 | Sipil et al. |
| 2010/0325954 A1 | 12/2010 | Tiwari et al. |

(56) References Cited

U.S. PATENT DOCUMENTS

| | | |
|---|---|---|
| 2011/0017443 A1 | 1/2011 | Collins |
| 2011/0067438 A1 | 3/2011 | Bernasconi |
| 2011/0068585 A1 | 3/2011 | Dube et al. |
| 2011/0113675 A1 | 5/2011 | Fujiyama et al. |
| 2011/0123407 A1 | 5/2011 | Freel |
| 2011/0132737 A1 | 6/2011 | Jadhav |
| 2011/0139597 A1 | 6/2011 | Lin |
| 2011/0146135 A1 | 6/2011 | Brandvold |
| 2011/0146140 A1 | 6/2011 | Brandvold et al. |
| 2011/0146141 A1 | 6/2011 | Frey et al. |
| 2011/0146145 A1 | 6/2011 | Brandvold et al. |
| 2011/0160505 A1 | 6/2011 | McCall |
| 2011/0182778 A1 | 7/2011 | Breton et al. |
| 2011/0201854 A1 | 8/2011 | Kocal et al. |
| 2011/0224471 A1 | 9/2011 | Wormsbecher et al. |
| 2011/0239530 A1 | 10/2011 | Marinangeli et al. |
| 2011/0253600 A1 | 10/2011 | Niccum |
| 2011/0258914 A1 | 10/2011 | Banasiak et al. |
| 2011/0284359 A1 | 11/2011 | Sechrist et al. |
| 2012/0012039 A1 | 1/2012 | Palmas et al. |
| 2012/0017493 A1 | 1/2012 | Traynor et al. |
| 2012/0022171 A1 | 1/2012 | Frey |
| 2012/0023809 A1 | 2/2012 | Koch et al. |
| 2012/0047794 A1 | 3/2012 | Bartek et al. |
| 2012/0137939 A1 | 6/2012 | Kulprathipanja |
| 2012/0160741 A1 | 6/2012 | Gong et al. |
| 2012/0167454 A1 | 7/2012 | Brandvold et al. |
| 2012/0172622 A1 | 7/2012 | Kocal |
| 2012/0205289 A1 | 8/2012 | Joshi |
| 2012/0214114 A1 | 8/2012 | Kim et al. |
| 2012/0216448 A1 | 8/2012 | Ramirez Corredores et al. |
| 2012/0279825 A1 | 11/2012 | Freel et al. |
| 2012/0317871 A1 | 12/2012 | Frey et al. |
| 2013/0029168 A1 | 1/2013 | Trewella et al. |
| 2013/0062184 A1 | 3/2013 | Kulprathipanja et al. |
| 2013/0067803 A1 | 3/2013 | Kalakkunnath et al. |
| 2013/0075072 A1 | 3/2013 | Kulprathipanja et al. |
| 2013/0078581 A1 | 3/2013 | Kulprathipanja et al. |
| 2013/0105356 A1 | 5/2013 | Dijs et al. |
| 2013/0109765 A1 | 5/2013 | Jiang et al. |
| 2013/0118059 A1 | 5/2013 | Lange et al. |
| 2013/0150637 A1 | 6/2013 | Borremans et al. |
| 2013/0152453 A1 | 6/2013 | Baird et al. |
| 2013/0152454 A1 | 6/2013 | Baird et al. |
| 2013/0152455 A1 | 6/2013 | Baird et al. |
| 2013/0195727 A1 | 8/2013 | Bull et al. |
| 2013/0212930 A1 | 8/2013 | Naae et al. |
| 2013/0267743 A1 | 10/2013 | Brandvold et al. |
| 2014/0001026 A1 | 1/2014 | Baird et al. |
| 2014/0140895 A1 | 5/2014 | Davydov et al. |
| 2014/0142362 A1 | 5/2014 | Davydov et al. |

FOREIGN PATENT DOCUMENTS

| | | |
|---|---|---|
| CA | 1312497 | 1/1993 |
| CA | 2091373 | 9/1997 |
| CA | 2299149 | 12/2000 |
| CA | 2521829 | 3/2006 |
| CN | 1377938 | 11/2002 |
| CN | 1730177 | 2/2006 |
| CN | 101045524 | 10/2007 |
| CN | 101238197 | 8/2008 |
| CN | 101294085 | 10/2008 |
| CN | 101318622 | 12/2008 |
| CN | 101353582 | 1/2009 |
| CN | 101365770 | 2/2009 |
| CN | 101381611 | 3/2009 |
| CN | 101544901 | 9/2009 |
| CN | 101550347 | 10/2009 |
| CN | 101745349 | 6/2010 |
| CN | 101993712 | 3/2011 |
| EP | 105980 | 1/1986 |
| EP | 578503 | 1/1994 |
| EP | 676023 | 7/1998 |
| EP | 718392 | 9/1999 |
| EP | 787946 | 6/2000 |
| EP | 1420058 | 5/2004 |
| EP | 2325281 | 5/2011 |
| FI | 117512 | 11/2005 |
| FR | 879606 | 3/1943 |
| GB | 1019133 | 2/1966 |
| GB | 1300966 | 12/1972 |
| JP | 58150793 | 9/1983 |
| JP | 1277196 | 11/1989 |
| JP | 11148625 | 6/1999 |
| JP | 2001/131560 | 5/2001 |
| JP | 2007/229548 | 9/2007 |
| SE | 9903742-6 | 1/2004 |
| WO | 81/01713 | 6/1981 |
| WO | 91/11499 | 8/1991 |
| WO | 92/07842 | 5/1992 |
| WO | 92/18492 | 10/1992 |
| WO | 94/13827 | 6/1994 |
| WO | 97/44410 | 11/1997 |
| WO | 01/09243 | 2/2001 |
| WO | 01/83645 | 11/2001 |
| WO | 02/49735 | 6/2002 |
| WO | 2006/071109 | 7/2006 |
| WO | 2007/017005 | 2/2007 |
| WO | 2007/045093 | 4/2007 |
| WO | 2007/050030 | 5/2007 |
| WO | 2007/112570 | 10/2007 |
| WO | 2007/128798 | 11/2007 |
| WO | 2008/009643 | 1/2008 |
| WO | 2008/020167 | 2/2008 |
| WO | 2008/092557 | 8/2008 |
| WO | 2009/019520 | 2/2009 |
| WO | 2009/047387 | 4/2009 |
| WO | 2009/047392 | 4/2009 |
| WO | 2009/067350 | 5/2009 |
| WO | 2009/099684 | 8/2009 |
| WO | 2009/118357 | 10/2009 |
| WO | 2009/118363 | 10/2009 |
| WO | 2009/126508 | 10/2009 |
| WO | 2009/131757 | 10/2009 |
| WO | 2010/002792 | 1/2010 |
| WO | 2011/146262 | 11/2011 |
| WO | 2012/009207 | 1/2012 |
| WO | 2012/012260 | 1/2012 |
| WO | 2012/062924 | 5/2012 |
| WO | 2012/078422 | 6/2012 |
| WO | 2012/088546 | 6/2012 |
| WO | 2012/115754 | 8/2012 |
| WO | 2013/043485 | 3/2013 |
| WO | 2013/090229 | 6/2013 |
| WO | 2014/031965 | 2/2014 |
| WO | 2014/210150 | 12/2014 |

OTHER PUBLICATIONS

Daoust et al. "Canada Yew (*Taxus canadensis Marsh.*) and Taxanes: a Perfect Species for Field Production and Improvement through Genetic Selection," Natural Resources Canada, Canadian Forest Service, Sainte-Fov, Quebec (2003).

Holton et al. "First Total Synthesis of Taxol. 2. Completion of the C and D Rings," *J Am Chem Soc*, 116 (1994) 1599-1600.

Huang et al. "New Taxanes from *Taxus brevifolia*," *J of Natural Products*, 49 (1986) 665-669.

Huie, C. W. "A review of modern sample-preparation techniques for the extraction and analysis of medicinal plants," *Anal Bioanal Chem*, 373 (2002) 23-30.

Kingston et al. "New Taxanes from *Taxus brevifolia*," *J of Natural Products*, 45 (1982) 466-470.

McLaughlin et al. 19-Hydroxybaccatin III, 10-Deacetylcephalo-Mannine, and 10-Deacetyltaxol: New Anti-Tumor Taxanes from *Taxus wallichiana*, *J of Natural Products*, 44 (1981) 312-319.

McNeil "Semisynthetic Taxol Goes on Market Amid Ongoing Quest for New Versions," *J of the National Cancer Institute*, 87:15 (1995) 1106-1108.

Miller et al. "Antileukemic Alkaloids from *Taxus wallichiana Zucc*," *J Org Chem*, 46 (1981) 1469-1474.

Newton "Taxol: A Case Study in Natural Products Chemistry," Lecture Notes, University of Southern Maine, http:/www.usm.maine.edu/ (2009) 1-6.

(56) References Cited

OTHER PUBLICATIONS

Nicolaou et al. "Total Synthesis of Taxol," *Nature*, 367 (1994) 630-634.
Ong et al. "Pressurized hot water extraction of bioactive or marker compounds in botanicals and medicinal plant materials," *J Chromatography A*, 1112 (2006) 92-102.
Pavia et al., Intro to Org Labo Techniques (1988) 3d ed. Saunders College Publishing, Washington p. 62-66, 541-587.
Rao "Taxol and Related Taxanes. I. Taxanes of *Taxus brevifolia* Bark," *Pharm Res* 10:4 (1993) 521-524.
Rao et al. "A New Large-Scale Process for Taxol and Related Taxanes from *Taxus brevifolia*," *Pharm Res*, 12:7 (1995) 1003-1010.
Senilh et al. "Mise en Evidence de Nouveaux Analogues du Taxol Extraits de *Taxus baccata*," *J of Natural Products*, 47 (1984) 131-137. (English Abstract included).
Smith R.M. "Extractions with superheated water," *J Chromatography A*, 975 (2002) 31-46.
Snader "Detection and Isolation," in Suffness, M. (ed) *Taxol-Science and Applications*, CRC Press, Boca Raton, Florida (1995) 277-286.
Stierle et al. "The Search for Taxol-Producing Microorganism Among the Endophytic Fungi of the Pacific Yew, *Taxus brevifolia*," *J of Natural Products*, 58 (1995) 1315-1324.
Yukimune et al. "Methyl Jasmonate-induced Overproduction of Paclitaxel and Baccatin III in Taxus Cell Suspension Cultures," *Nature Biotechnology* 14 (1996) 1129-1132.
Office Action for Chinese Patent Application No. 200780020439.9, issued Oct. 13, 2010.
English Translation of Office Action for Chinese Patent Application No. 200780020439.9, issued Oct. 13, 2010.
Office Action Mailed Jan. 10, 2014 in corresponding Chinese Patent Application No. 201210096487.9 (English translation provided).
AccessScience Dictionary, "ebullating-bed reactor," http://www.accessscience.com, last visited Jul. 15, 2014.
Adam, J. "Catalytic conversion of biomass to produce higher quality liquid bio-fuels," *PhD Thesis*, Department of Energy and Process Engineering, The Norwegian University of Science and Technology, Trondheim (2005).
Adam, J. et al. "Pyrolysis of biomass in the presence of AI-MCM-41 type catalysts," *Fuel*, 84 (2005) 1494-1502.
Adjaye, John D. et al. "Catalytic conversion of a biomass-derived oil to fuels and chemicals I: Model compound studies and reaction pathways," *Biomass & Bioenergy*, 8:3 (1995) 131-149.
Adjaye, John D. et al. "Catalytic conversion of a biomass-derived oil to fuels and chemicals II: Chemical kinetics, parameter estimation and model predictions," *Biomass & Bioenergy*, 8:4 (1995) 265-277.
Adjaye, John D. et al. "Catalytic conversion of wood derived bio-oil to fuels and chemicals," *Studies in Surface Science and Catalysis*, 73 (1992) 301-308.
Adjaye, John D. et al. "Production of hydrocarbons by the catalytic upgrading of a fast pyrolysis bio-oil," *Fuel Process Technol*, 45:3 (1995) 161-183.
Adjaye, John D. et al. "Upgrading of a wood-derived oil over various catalysts," *Biomass & Bioenergy*, 7:1-6 (1994) 201-211.
Aho, A. et al. "Catalytic pyrolysis of woody biomass in a fluidized bed reactor; Influence of zeolites structure, Science Direct," *Fuel*, 87 (2008) 2493-2501.
Antonakou, E. et al. "Evaluation of various types of AI-MCM-41 materials as catalysts in biomass pyrolysis for the production of bio-fuels and chemicals," *Fuel*, 85 (2006) 2202-2212.
Atutxa, A. et al. "Kinetic Description of the Catalytic Pyrolysis of Biomass in a Conical Spouted Bed Reactor," *Energy Fuels*, 19:3 (2005) 765-774.
Baker, E. G. et al. "Catalytic Upgrading of Biomass Pyrolysis Oils," in Bridgwater, A. V. et al. (eds) *Research in Thermochemical Biomass Conversion*, Elsevier Science Publishers Ltd., Barking, England (1988) 883-895.

Baldauf, W. et al. "Upgrading of flash pyrolysis oil and utilization in refineries," *Biomass & Bioenergy*, 7 (1994) 237-244.
Baumlin, "The continuous self stirred tank reactor: measurement of the cracking kinetics of biomass pyrolysis vapours," *Chemical Engineering Science*, 60 (2005) 41-55.
Berg, "Reactor Development for the Ultrapyrolysis Process," *The Canadian Journal of Chemical Engineering*, 67 (1989) 96-101.
Bielansky, P. et al. "Catalytic conversion of vegetable oils in a continuous FCC pilot plant," *Fuel Processing Technology*, 92 (2011) 2305-2311.
Bimbela, F. et al. "Hydrogen production by catalytic steam reforming of acetic acid, a model compound of biomass pyrolysis liquids," *J. Ana App. Pyrolysis*, 79 (2007) 112-120.
Bridgwater et al. (eds) *Fast Pyrolysis of Biomass: A Handbook*, Newbury Cpl Press, Great Britain (2002) 12-13.
Bridgwater, A.V. "Principles and practices of biomass fast pyrolysis processes for liquids," *Journal of Analytical and Applied Pyrolysis*, 51 (1999) 3-22.
Bridgwater, Tony "Production of high grade fuels and chemicals from catalytic pyrolysis of biomass," *Catalysis Today*, 29 (1996) 285-295.
Bridgwater, Tony et al. "Transport fuels from biomass by thermal processing," *EU-China Workshop on Liquid Biofuels*, Beijing, China (Nov. 4-5, 2004).
Buchsbaum, A. et al. "The Challenge of the Biofuels Directive for a European Refinery," *OMW Refining and Marketing, ERTC 9th Annual Meeting*, Prague, Czech Republic (Nov. 15-17, 2004).
Carlson, T. et al. "Aromatic Production from Catalytic Fast Pyrolysis of Biomass-Derived Feedstocks," *Top Catal*, 52 (2009) 241-242.
Carlson., T. et al. "Green Gasoline by Catalytic Fast Pyrolysis of Solid Biomass Derived Compounds," *ChemSusChem*, 1 (2008) 397-400.
Chantal, P. D. et al. "Production of Hydrocarbons from Aspen Poplar Pyrolytic Oils over H-ZSM5," *Applied Catalysis*, 10 (1984) 317-332.
Chen, N. Y. et al. "Fluidized Upgrading of Wood Pyrolysis Liquids and Related Compounds," in Soltes, E. J. et al. (eds) *Pyrolysis Oils from Biomass*, ACS, Washington, DC (1988) 277-289.
Chinsuwan, A. et al. "An experimental investigation of the effect of longitudinal fin orientation on heat transfer in membrane water wall tubes in a circulating fluidized bed," *International Journal of Heat and Mass Transfer*, 52:5-6 (2009) 1552-1560.
Cornelissen, T. et al., "Flash co-pyrolysis of biomass with polylactic acid. Part 1: Influence on bio-oil yield and heating value," *Fuel* 87 (2008) 1031-1041.
Cousins, A. et al. "Development of a bench-scale high-pressure fluidized bed reactor and its sequential modification for studying diverse aspects of pyrolysis and gasification of coal and biomass," *Energy and Fuels*, 22:4 (2008) 2491-2503.
Czernik, S. et al. "Hydrogen from biomass-production by steam reforming of biomass pyrolysis oil," *Catalysis Today*, 129 (2007) 265-168.
Czernik, S. et al. "Hydrogren by Catalytic Steam Reforming of Liquid Byproducts from Biomass Thermoconversion Processes," *Ind. Eng. Chem. Res.*, 41 (2002) 4209-4215.
Dahmen, "Rapid pyrolysis for the pretreatment of biomass and generation of bioslurry as intermediate fuel", *Chemie- Ingenieur-Technik*, 79:9 (2007) 1326-1327. Language: German (Abstract only; Machine translation of Abstract).
Dandik, "Catalytic Conversion of Used Oil to Hydrocarbon Fuels in a Fractionating Pyrolysis Reactor," *Energy & Fuels*, 12 (1998) 1148-1152.
de Wild, P. et al. "Lignin valorisation for chemicals and (transportation) fuels via (catalytic) pyrolysis and hydrodeoxygenation," *Environ. Prog. Sustainable Energy*, 28 (2009) 461-469.
Demirbas, Ayhan "Fuel Conversional Aspects of Palm Oil and Sunflower Oil," *Energy Sources*, 25 (2003) 457-466.
Di Blasi, C. et al. "Effects of Potassium Hydroxide Impregnation of Wood Pyrolysis, American Chemical Society," *Energy & Fuels* 23 (2009) 1045-1054.
Ellioti, D. "Historical Developments in Hydroprocessing Bio-oils," *Energy & Fuels*, 21 (2007) 1792-1815.

(56) References Cited

OTHER PUBLICATIONS

Ensyn Technologies Inc. "Catalytic de-oxygenation of biomass-derived RTP vapors." Prepared for ARUSIA, Agenzia Regionale Umbria per lo Sviluppo e L'Innovazione, Perugia, Italy (Mar. 1997).
Filtration, Kirk-Othmer Encyclopedia of Chemical Technology 5th Edition. vol. 11., John Wiley & Sons, Inc., Feb. 2005.
Gayubo, A. G. et al. "Deactivation of a HZSM-5 Zeolite Catalyst in the Transformation of the Aqueous Fraction of Biomass Pyrolysis Oil into Hydrocarbons," Energy & Fuels, 18:6 (2004) 1640-1647.
Gayubo, A. G. et al. "Undesired components in the transformation of biomass pyrolysis oil into hydrocarbons on an HZSM-5 zeolite catalyst," J Chem Tech Biotech, 80 (2005) 1244-1251.
Geyert Bërjie S. et al. "Upgrading of directly liquefied biomass to transportation fuels: catalytic cracking," Biomass 14:3 (1987) 173-183.
Goesele, W. et al., Filtration, Wiley-VCHVerlag GmbH & Co. KGaA, Weinheim, 10.1002/14356007.b0210, 2005.
Graham, R.G. et al. "Thermal and Catalytic Fast Pyrolysis of Lignin by Rapid Thermal Processing (RPT)," Seventh Canadian Bioenergy R&D Seminar, Skyline Hotel, Ottawa, Ontario, Canada, Apr. 24-26, 1989.
Grange, P. et al. "Hydrotreatment of pyrolysis oils from biomass: reactivity of the various categories of oxygenated compounds and preliminary techno-economical study," Catalysis Today, 29 (1996) 297-301.
Hama, "Biodiesel-fuel production in a packed-bed reactor using lipase-producing Rhizopus oryzae cells immobilized within biomass support particles", Biochemical Engineering Journal, 34 (2007) 273-278.
Hoekstra, E. et al., "Fast Pyrolysis of Biomass in a Fluidized Bed Reactor: In Situ Filtering of the Vapors," Ind. Eng. Chern. Res., 48:10 (2009) 4744-4756.
Horne, Patrick A. et al. "Catalytic coprocessing of biomass-derived pyrolysis vapours and methanol," J. Analytical and Applied Pyrolysis, 34:1 (1995) 87-108.
Horne, Patrick A. et al. "Premium quality fuels and chemicals from the fluidised bed pyrolysis of biomass with zeolite catalyst upgrading," Renewable Energy, 5:5-8 (1994) 810-812.
Horne, Patrick A. et al. "The effect of zeolite ZSM-5 catalyst deactivation during the upgrading of biomass-derived pyrolysis vapours," J Analytical and Applied Pyrolysis, 34:1 (1995) 65-85.
Huffman, D. R. et al., Ensyn Technologies Inc., "Thermo-Catalytic Cracking of Wood to Transportation Fuels," DSS Contract No. 38SQ.23440-4-1429, Efficiency and Alternative Energy Technology Branch, Natural Resources Canada, Ottawa, Canada (1997).
Huffman, D. R., Ensyn Technologies Inc., "Thermo-catalytic cracking of wood to transportation fuels using the RTP process," DSS Contract No. 38SQ.23440-4-1429, Efficiency and Alternative Energy Technology Branch, Natural Resources Canada, Ottawa, Ontario (Jan. 1997).
Hughes, J. et al. "Structural variations in natural F, OH and CI apatites," American Mineralogist, 74 (1989) 870-876.
International Search Report dated Feb. 22, 2013 for corresponding International Application No. PCT/US2012/68876.
Ioannidou, "Investigating the potential for energy, fuel, materials and chemicals production from corn residues (cobs and stalks) by non-catalytic and catalytic pyrolysis in two reactor configurations," Renewable and Sustainable Energy Reviews, 13 (2009) 750-762.
Iojoiu, E. et al. "Hydrogen production by sequential cracking of biomass-derived pyrolysis oil over noble metal catalysts supported on ceria-zirconia," Applied Catalysis A: General, 323 (2007) 147-161.
Jackson, M. et al. "Screening heterogenous catalysts for the pyrolysis of lignin," J. Anal. Appl. Pyrolysis, 85 (2009) 226-230.
Junming et al. "Bio-oil upgrading by means of ethyl ester production in reactive distillation to remove water and to improve storage and fuel characteristics," Biomass and Energy, 32 (2008) 1056-1061.
Kalnes, Tom et al. "Feedstock Diversity in the Refining Industry," UOP Report to NREL and DOE (2004).
Khanal, "Biohydrogen Production in Continuous-Flow Reactor Using Mixed Microbial Culture," Water Environment Research, 78:2 (2006) 110-117.
Khimicheskaya Entsiklopediya. Pod red. N. S. Zefirov. Moskva, Nauchnoe Izdatelstvo "Bolshaya Rossyskaya Entsiklopediya", 1995, p. 133-137,529-530.
Lappas, A. A. et al. "Biomass pyrolysis in a circulating fluid bed reactor for the production of fuels and chemicals," Fuel, 81 (2002) 2087-2095.
Lappas, A.A. et al. "Production of Transportation Fuels from Biomass," Workshop of Chemical Process Engineering Research Institute/Center for Research and Technology Hellas, Thermi-Thessaloniki, Greece (2004).
Lappas, A.A., "Production of biofuels via co-processing in conventional refining process," Catalysis Today, 145 (2009) 55-62.
Maiti, R.N. et al. "Gas-liquid distributors for trickle-bed reactors: A review"; Industrial and Engineering Chemistry Research, 46:19 (2007) 6164-6182.
Mancosky, "The use of a controlled cavitation reactor for bio-diesel production," (abstract only), AIChE Spring National Meeting 2007, Houston, Texas.
Marker, Terry L., et al. "Opportunities for Biorenewables in Petroleum Refineries," Proceedings of the 230th ACS National Meeting, Washington, DC, Paper No. 125, Fuel Division (Aug. 31, 2005) (abstract only).
Marker, Terry L., et al., UOP, "Opportunities for Biorenewables in Oil Refineries," Final Technical Report, U.S. Department of Energy Award No. DE-FG36-05G015085, Report No. DOEGO15085Final (2005).
Marquevich, "Hydrogen from Biomass: Steam Reforming of Model Compounds of Fast-Pyrolysis Oil," Energy & Fuels, 13 (1999) 1160-1166.
Masoumifard, N. et al. "Investigation of heattransfer between a horizontal tube and gas-solid ftuidized bed," International Journal of Heat and Fluid Flow, 29:5 (2008) 1504-1511.
Meier, D. et al. "State of the art of applied fast pyrolysis of lignocellulosic materials—a review," Bioresource Technology, 68:1 (1999) 71-77.
Meier, D. et al., "Pyrolysis and Hydroplysis of Biomass and Lignins—Activities at the Institute of Wood Chemistry in Hamburg, Germany," vol. 40, No. 2, Preprints of Papers Presented at the 209th ACS National Meeting, Anaheim, CA (Apr. 2-7, 1995).
Mercader, F. et al. "Pyrolysis oil upgrading by high pressure thermal treatment," Fuel, 89:10 (2010) 2829-2837.
Mohan, D. et al. "Pyrolysis of Wood/Biomass for Bio-oil: A Critical Review," Energy Fuels, 20:3 (2006) 848-849.
Nowakowski, D. et al. "Potassium catalysis in the pyrolysis behaviour of short rotation willow coppice," Fuels, 86 (2007) 2389-2402.
Ognisty, T. P. "The direct contact heat transfer performance of a spray nozzle, a notched through distributor, and two inch Pall rings," AIChE 1990 Spring National Meeting (Orlando 3/18-22-90) Preprint N. 37c 36P, Mar. 18, 1990.
Ohman "Bed Agglomeration Characteristics during Fluidized Bed Combustion of Biomass Fuels," Energy & Fuels, 14 (2000) 169-178.
Okumura, Y. et al. "Pyrolysis and gasification experiments of biomass under elevated pressure condition," Nihon Kikai Gakkai Ronbunshu, B Hen/Transactions of the Japan Society of Mechanical Engineers, Part B, vol. 73, No. 7, 2007, pp. 1434-1441.
Olazar, M. et al. "Pyrolysis of Sawdust in a Conical Spouted-Bed Reactor with a HZSM-5 Catalyst," AIChE Journal, 46:5 (2000) 1025-1033.
Onay "Influence of pyrolysis temperature and heating rate on the production of bio-oil and char from safflower seed by pyrolysis, using a well-swept fixed-bed reactor," Fuel Processing Technology, 88 (2007) 523-531.
Onay, "Production of Bio-Oil from BiomaSs: Slow Pyrolysis of Rapeseed (Brassica napus L.) in a Fixed-Bed Reactor," Energy Sources, 25 (2003) 879-892.
Ooi, Y. S. et al. "Catalytic Cracking of Used Palm Oil and Palm Oil Fatty Acids Mixture for the Production of Liquid Fuel: Kinetic Modeling." J Am Chem Soc, 18 (2004) 1555-1561.

(56) References Cited

OTHER PUBLICATIONS

Otterstedt, J. E. et al. "Catalytic Cracking of Heavy Oils," in Occelli, Mario L. (ed) Fluid Catalytic Cracking, Chapter 17, ACS, Washington, DC (1988) 266-278.

Padmaja, K.V. et al. "Upgrading of Candelilla biocrude to hydrocarbon fuels by fluid catalytic cracking," *Biomass and Bioenergy*, 33 (2009) 1664-1669.

PCT/US2012/055384 International Search Report, dated Mar. 28, 2013, and International Preliminary Report on Patentability, dated Mar. 25, 2014.

Pecora, A.A.B. et al., "Heat transfer coefficient in a shallow fluidized bed heat exchanger with a continuous flow of solid particles," *Journal of the Brazilian Society of Mechanical Sciences and Engineering*, 28:3 (2006) 253-258.

Pecora, A.A.B., et al., "An analysis of process heat recovery in a gas-solid shallow fluidized bed," *Brazilian Journal of Chemical Engineering*, 23:4 (2006) 497-506.

Petrik, P.T. et al. "Heat exchange in condensation of R227 coolant on inclined tubes placed in a granular Bed," *Journal of Engineering Physics and Thermophysics*, 77:4 (2004) 758-761.

Prasad Y. S. et al. "Catalytic conversion of canola oil to fuels and chemical feedstocks. Part II. Effect of co-feeding steam on the performance of HZSM-5 catalyst," *Can J Chem Eng*, 64 (1986) 285-292.

Prins, Wolter et al. "Progress in fast pyrolysis technology," *Topsoe Catalysis Forum* 2010, Munkerupgaard, Denmark (Aug. 19-20, 2010).

Radlein, D. et al. "Hydrocarbons from the Catalytic Pyrolysis of Biomass," *Energy & Fuels*, 5 (1991) 760-763.

Ravindranath, G., et al., "Heat transfer studies of bare tube bundles in gas-solid fluidized bed", 9th International Symposium on Fluid Control Measurement and Visualization 2007, FLUCOME 2007, vol. 3, 2007, pp. 1361-1369.

Rodriguez, O.M.H. et al. "Heat recovery from hot solid particles in a shallow fluidized bed," *Applied Thermal Engineering*, 22:2 (2002) 145-160.

Samolada, M. C. et al. "Production of a bio-gasoline by upgrading biomass flash pyrolysis liquids via hydrogen processing and catalytic cracking," *Fuel*, 77:14 (1998) 1667-1674.

Sang "Biofuel Production from Catalytic Cracking of Palm Oil," *Energy Sources*, 25 (2003) 859-869.

Scahill, J. et al. " Removal of Residual Char Fines from Pyrolysis Vapors by Hot Gas Filtration," in Bridgwater, A. V. et al. (eds) *Developments in Thermochemical Biomass Conversion*, Springer Science+Business Media, Dordrecht (1997) 253-266.

Scott, D. et al. Pretreatment of poplar wood for fast pyrolysis: rate of cation removal, *Journal of Analytical and Applied Pyrolysis*, 57 (2000) 169-176.

Sharma, R. "Upgrading of pyrolytic lignin fraction of fast pyrolysis oil to hydrocarbon fuels over HZSM-5 in a dual reactor system," *Fuel Processing Technology*, 35 (1993) 201-218.

Sharma, R. K. et al. "Catalytic Upgrading of Pyrolysis Oil," *Energy & Fuels*, 7 (1993) 306-314.

Sharma, R. K. et al. "Upgrading of wood-derived bio-oil over HZSM-5," *Bioresource Technology*, 35:1 (1991) 57-66.

Srinivas, S.T. et al "Thermal and Catalytic Upgrading of a Biomass-Derived Oil in a Dual Reaction System." *Can. J. Chem. Eng.*, 78 (2009) 343-354.

Stojanovic, B. et al. "Experimental investigation of thermal conductivity coefficient and heat exchange between fluidized bed and inclined exchange surface," *Brazilian Journal of Chemical Engineering*, 26:2 (2009) 343-352.

Sukhbaatar, B. "Separation of Organic Acids and Lignin Fraction From Bio-Oil and Use of Lignin Fraction in Phenol-Formaldehyde Wood Adhesive Resin," *Master's Thesis*, Mississippi State (2008).

Twaiq, A. A. et al. "Performance of composite catalysts in palm oil cracking for the production of liquid fuels and chemicals," *Fuel Processing Technology*, 85 (2004) 1283-1300.

Twaiq, F. A. et al. "Liquid hydrocarbon fuels from palm oil by catalytic cracking over aluminosilicate mesoporous catalysts with various Si/Al ratios," *Microporous and Mesoporous Materials*, 64 (2003) 95-107.

Tyson, K. et al. "Biomass Oil Analysis: Research Needs and Recommendations," National Renewable Energy Laboratory, Report No. NREL/TP-510-34796 (Jun. 2004).

Valle, B. et al. "Integration of Thermal Treatment and Catalytic Transformation for Upgrading Biomass Pyrolysis Oil," *International Journal of Chemical Reactor Engineering*, 5:1 (2007).

Vasanova, L.K. "Characteristic features of heat transfer of tube bundles in a cross water-air flow and a three-phase fluidized bed," *Heat Transfer Research*, 34:5-6 (2003) 414-420.

Vitolo, S. et al. "Catalytic upgrading of pyrolytic oils over HZSM-5 zeolite: behaviour of the catalyst when used in repeated upgrading—regenerating cycles," *Fuel*, 80 (2001) 17-26.

Vitolo, S. et al. "Catalytic upgrading of pyrolytic oils to fuel over different zeolites," *Fuel*, 78:10 (1999) 1147-1159.

Wang, Xianhua et al., "The Influence of Microwave Drying on Biomass Pyrolysis," *Energy & Fuels* 22 (2008) 67-74.

Westerhof, Roel J. M. et al., "Controlling the Water Content of Biomass Fast Pyrolysis Oil," *Ind. Eng. Chem.* 46 (2007) 9238-9247.

Williams, Paul T. et al. "Characterisation of oils from the fluidised bed pyrolysis of biomass with zeolite catalyst upgrading," *Biomass and Bioenergy*, 7:1-6 (1994) 223-236.

Williams, Paul T. et al. "Comparison of products from the pyrolysis and catalytic pyrolysis of rice husks," *Energy*, 25:6 (2000) 493-513.

Williams, Paul T. et al. "The influence of catalyst type on the composition of upgraded biomass pyrolysis oils," *J Analytical and Applied Pyrolysis*, 31 (1995) 39-61.

Zhang et al. "Investigation on initial stage of rapid pyrolysis at high pressure using Taiheiyo coal in dense phase," *Fuel*, 81:9 (2002) 1189-1197.

Zhang, "Hydrodynamics of a Novel Biomass Autothermal Fast Pyrolysis Reactor: Flow Pattern and Pressure Drop," *Chem. Eng. Technol.*, 32:1 (2009) 27-37.

Bridgwater et al. (eds) *Fast Pyrolysis of Biomass: A Handbook*, Newbury Cpl Press, Great Britain (2008) 1-13.

Wisner, R. "Renewable Identification Nos. (RINs) and Government Biofuels Blending Mandates," *AgMRC Renewable Energy Newsletter* (Apr. 2009), available at http://www.agmrc.org/renewable_energy/biofuelsbiorefining_general/renewable-identification-numbers-rins-and-government-biofuels-blending-mandates/.

Qi et al. "Review of biomass pyrolysis oil properties and upgrading research," Energy Conversion & Management, 48 (2007) 87-92.

Yoo et al. "Thermo-mechanical extrusion pretreatment for conversion of soybean hulls to fermentable sugars," Bioresource Technology, 102 (2011) 7583-7590.

\* cited by examiner

THERMAL EXTRACTION METHOD AND PRODUCT

CROSS REFERENCE TO RELATED APPLICATIONS

This application is a continuation of U.S. patent application Ser. No. 12/295,916, which is the U.S. National Phase of International Application No. PCT/CA2007/000535, filed Apr. 2, 2007, which was published in English, and which further claims the benefit of priority from U.S. Provisional Application No. 60/788,045, filed Apr. 3, 2006. The foregoing related applications, in their entirety, are incorporated herein by reference.

The present invention relates to a method of producing an extract by thermal extraction, and a thermal extraction product.

BACKGROUND

Extraction of a desired compound from a source is commonly performed by solvent extraction methods.

Solvent extraction is used today on a number of starting materials, including biomass, to extract desired components. A good example of this is the extraction of taxanes from biomass.

Taxanes are a group of diterpenoid compounds, some of which have been demonstrated to be useful in the treatment of cancer and other serious diseases, such as multiple sclerosis and kidney disease. In particular, the taxane compounds paclitaxel, docetaxel, Baccatin III, 10-O-deacetylbaccatin III (10-DAB or DAB), 13-acetyl-9-dihydrobaccatin III (DHB), cephalomannine, and prostratin have been identified as useful in pharmaceutical applications. For instance, paclitaxel, is currently being used in cancer treatment (marketed as TAXOL® by Bristol-Myers Squibb). Certain taxanes, such as paclitaxel and docetaxel, can be used directly in pharmaceutical applications, without additional chemical modification, while other taxanes (DAB and DHB, for example) are viewed as precursors for the production of other taxanes such as paclitaxel and docetaxel.

The major sources of taxanes are the bark, needles and clippings of the yew (hemlock) tree, which belongs to the genus *Taxus*. Unfortunately, even though taxanes are more concentrated in yew than in other species of trees, the absolute concentrations are very low. For example, it has been reported that in a typical sample, yields of only 0.01% of paclitaxel are obtained from the bark of the yew tree, and in the range of from 0.003 to 0.015 percent (dry basis) of paclitaxel from the clippings and needles (Huang et al., J. Nat. Prod., 49:665, 1986.) where the first extraction is a solvent extraction. Furthermore, the yew tree is relatively rare and grows quite slowly, raising valid concerns that reforestation and resource management cannot keep up with the demand. Although synthetic and semi-synthetic pathways for producing paclitaxel have been devised, they are extremely complex and generally too costly for commercial production. Semi-synthetic processes have also been devised for producing docetaxel.

Current methods of commercial paclitaxel and other taxane production are complex and costly. The unit operations are predominantly physical methods involving: harvesting/collection, grinding, mulching, preliminary solvent extraction and separation to get a crude taxane product. Once the crude taxane product is produced, paclitaxel may be recovered and purified in additional solvent extractions and other refining steps. In many cases, the other natural taxanes are chemically converted to additional yields of paclitaxel or to docetaxel.

Current methods for isolating other compounds from starting materials also often include an initial step of solvent extraction, which removes a large amount of impurities together with the desired compounds. As a result, one or more liquid partitioning steps to enrich the concentrations of desired compounds in the extracts are often performed, followed in some cases by several chromatography steps.

A drawback of these methods is that they require large amounts of costly and, sometimes, toxic organic solvents for the extraction and partitioning steps. Commercially, this translates to very high capital and operating costs for materials, qualified expertise, qualified technical staffing, and infrastructure.

There is therefore a need for a method of isolating compounds, which method would reduce or eliminate the requirement of large amounts of toxic and costly organic solvents.

SUMMARY

According to one broad aspect of the invention, there is provided a method for producing a thermal extract by thermal extraction of a starting material, comprising: heating the starting material to a temperature and for a time sufficient to extract an amount of a desired compound from the starting material, without conversion of the desired compound into one or more other compounds in a substantial amount.

According to a further aspect of the invention, there is provided a method for obtaining a taxane-rich extract by thermal extraction.

In one exemplary embodiment of the invention, there is provided a method for producing a taxane-rich thermal extract from a diterpenoid-containing biomass starting material by thermal extraction of the biomass starting material, comprising: heating the biomass starting material to a temperature and for a time sufficient to extract an amount of taxanes, without conversion thereof into one or more other compounds in a substantial amount.

In an exemplary embodiment of the invention, there is provided a method for producing a thermal extract comprising a desired compound, comprising: introducing a starting material into a thermal extraction system comprising a contained vessel, a heat source, and at least one recovery unit; heating the starting material in the thermal extraction system to a temperature and for a time sufficient to produce a product stream comprising an amount of the desired compound, without conversion of the desired chemical compound into one or more other compounds in a substantial amount; and collecting at least one fraction from the product stream enriched in the desired compound in at least one of the at least one recovery units to obtain the thermal extract.

In a further exemplary embodiment of the invention, there is provided a method for producing a taxane-rich thermal extract from a diterpenoid-containing biomass starting material comprising: introducing the biomass starting material into a thermal extraction system comprising a contained vessel, a heat source, and at least one recovery unit; heating the biomass starting material in the thermal extraction system to a temperature and for a time sufficient to produce a product stream comprising an amount of taxanes, without conversion thereof into one or more other compounds in a substantial amount; and collecting at least one taxane-containing fraction from the product stream in at least one of the at least one recovery units to obtain the taxane-rich thermal extract.

According to another exemplary embodiment of the invention, there is provided a taxane-rich extract.

According to another exemplary embodiment of the invention, there is provided a terpene or terpenoid-rich thermal extract obtained by a method of the invention.

According to a still further exemplary embodiment of the invention, there is provided a taxane-rich thermal extract obtained by a method of the invention.

According to a further exemplary embodiment of the invention, there is provided a flavonoid-rich thermal extract obtained by a method of the invention.

According to another exemplary embodiment of the invention, there is provided an epicatechin-rich thermal extract obtained by a method of the invention.

According to another exemplary embodiment of the invention, there is provided a catechin-rich thermal extract obtained by a method of the invention.

According to another exemplary embodiment of the invention, there is provided a caffeine-rich thermal extract obtained by a method of the invention.

According to another exemplary embodiment of the invention, there is provided a vanillin-rich thermal extract obtained by a method of the invention.

According to another exemplary embodiment of the invention, there is provided a beta-sitosterol-rich thermal extract obtained by a method of the invention.

According to a yet further exemplary embodiment of the invention, there is provided an extract comprising paclitaxel and 10-O-deacetylbaccatin III, wherein the 10-O-deacetylbaccatin III is present in the extract in an amount that is approximately 10 times greater than an amount of the paclitaxel on a weight per weight basis.

According to a yet further exemplary embodiment of the invention, there is provided an extract comprising paclitaxel and 13-acetyl-9-dihydrobaccatin III, wherein the 13-acetyl-9-dihydrobaccatin III is present in the extract in an amount that is approximately 10 times greater than the amount of paclitaxel on a weight per weight basis.

According to a yet further exemplary embodiment of the invention, there is provided an extract comprising paclitaxel and 7-epi-taxol, wherein the 7-epi-taxol is present in the extract in an amount that is approximately 10 times greater than the paclitaxel on a weight per weight basis.

DETAILED DESCRIPTION

Figure 1:
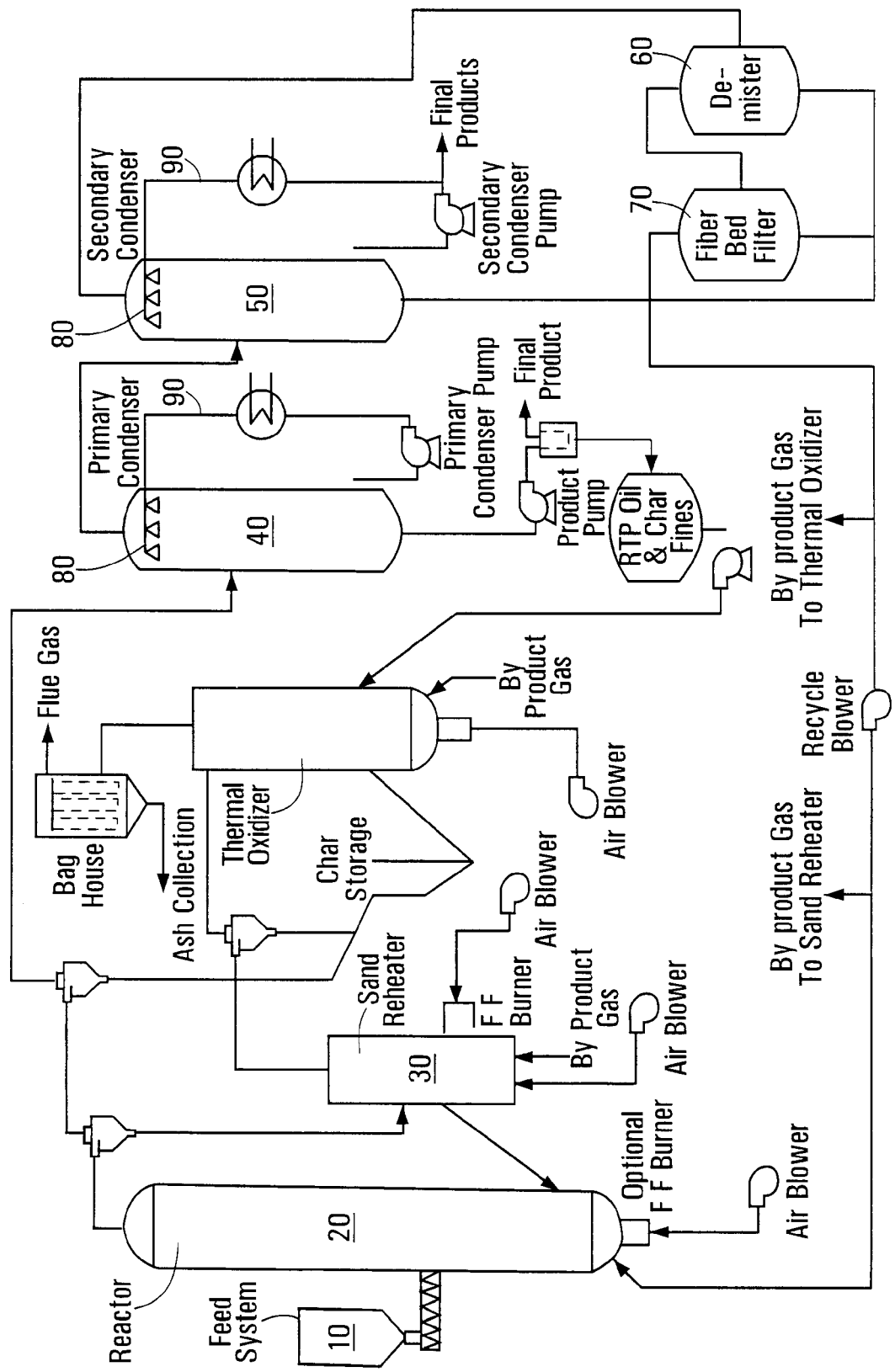
FIG. 1 is a schematic illustration of an example of a suitable thermal extraction system according to one embodiment of the invention.

It has been observed that thermal extraction can be used as an alternate means of extraction to solvent extraction.

An implication of thermal extraction is that the initial step of solvent extraction of a feedstock, as presently associated with solvent extraction methods, is not required.

By "thermal extraction" (which may also be referred to as "thermal distillation" or "rapid thermal distillation"), as used herein is meant an extraction method where heat is used to separate one or more desired compounds from suitable starting materials. By applying heat to suitable starting materials in a controlled manner in a contained (i.e., enclosed) environment, one or more desired compounds can be liberated, preserved, recovered, and left substantially undestroyed. Thermal extraction may therefore be used to extract a naturally occurring desired compound from a starting material, which naturally occurring compound was found in the starting material, without chemical conversion. While thermal extraction may destroy or chemically convert some compounds in the starting material, a substantial amount of the desired compound is not degraded or otherwise chemically altered. By "naturally occurring desired compound" or "desired compound" obtained by thermal extraction is meant a compound present in the starting material and where a substantial amount of this compound is not degraded or otherwise chemically converted into another compound by the thermal extraction method of the present invention.

The material that may be used in the present invention is not particularly limited, providing that it provides a source of the one or more desired compounds and it can be subjected to thermal extraction. For example, biomass is a common starting material for solvent extraction methods, and it may also be a suitable starting material for the methods of the present invention. The biomass may be, for example, derived from a plant. Any part of the plant may be suitable for thermal extraction, including the bark, needles, stems, roots, leaves, seeds, plant cells in culture, etc.; or a mixture thereof. Plant derived biomass material that is used in the present invention may be in, for example, a freshly harvested state, a dry state, or a hydrated state.

If one or more taxanes are the desired compounds, then diterpenoid-containing biomass materials such as those derived from the yew tree are generally considered an excellent source of taxanes. For example, all or various components of a species of the genus *Taxus* or *Austrotaxus* may be used as a taxanes source.

In another invention embodiment, thermal extraction may be used to extract flavonoids from suitable starting materials. Over five thousand naturally occurring flavonoids (including isoflavonoids and neoflavonoids) have been characterized from various plants. The thermal extraction method of the present invention can be used to extract some of these compounds from these biomass materials. Some of these compounds include, without limitation, quercetin, epicatechin, proanthocyanidins, citrus bioflavonoids, catechins, resveratrol, kaempferol vanillin and beta-sitosterol. In one embodiment of the present invention, epicatechin is extracted from cocoa or a cocoa containing starting material, for example. Flavonoids may be used, for instance, as antioxidants, as well as other uses, such as in treating or preventing cancer, heart disease, etc. Another source of flavonoids is, for example and without limitation, flax or a flax containing starting material. Flax may be used to obtain a thermal extract according to the invention comprising one or more flavonoids including catechins and epicatechin. Other natural products extracted from biomass might also be obtained by using thermal extraction, and used as medicines, natural supplements, etc. By way of another non-limiting example, a starting material comprising coffee could be used to obtain a thermal extract comprising caffeine.

It will be apparent to a person skilled in the art that any number of other materials may be suitable starting materials for obtaining a thermal extract comprising one or more desired compounds.

The starting material used in the present invention may also be reduced in size. For example, it may be shredded or ground by methods known in the art, prior to thermal extraction.

In one exemplary embodiment of the present invention, the material that is to be subjected to thermal extraction is first reduced in size to having an average diameter of less than about 2 cm in its smallest dimension. In another exemplary embodiment of the present invention, the starting material is first reduced in size to having an average diameter of less than about 1 cm in its smallest dimension.

Thermal extraction according to the invention may be carried out in a thermal extraction system, which system is not particularly limited. In a thermal extraction of the invention, all or a portion of the starting material may be exposed to heat in a controlled and contained environment. For instance, if the starting material is a biomass material, ligninic, cellulosic, or hemicellulosic fractions, or combinations thereof, could be used. By a controlled environment is meant an environment where heat is applied in such a manner as to cause a phase change or chemical conversion of the starting material but not in a manner that would cause a substantial amount of the desired compound present in the starting material to be adversely altered, degraded, destroyed, etc. For example, in one embodiment, the thermal extract comprises from about 0 to 10% w/w (or any subrange thereof) of impurities resulting from chemical or other conversion of the desired compound into another compound.

In one exemplary embodiment of the invention, the thermal extraction is carried out in a thermal extraction system comprising a contained vessel, a heat source and one or more recovery units. Thermal extraction may then be achieved by heat transfer to the starting material and any resulting intermediate product. The starting material and any resulting intermediate product may thus be heated to a sufficient temperature for a sufficient period of time to produce a product stream, fractions of which may then be recovered in the one or more recovery units, and collected to obtain an extract.

By way of example, the thermal extraction system may comprise a standard retort system (i.e., a fixed or moving bed either under vacuum or at pressure), a bubbling fluid bed, an upflow thermal extraction unit, a circulating fluid bed, a transported bed, an ablative thermal extraction unit, an entrained flow thermal extraction unit, a rotary kiln or a mechanical transport thermal extraction unit (e.g., heated auger system).

Any device that collects product vapours and liquids produced during thermal extraction may be used as a recovery unit. A recovery unit may include a condenser. The condenser may be a contact or surface condenser that cools and collects a liquid product from a vapour, or a liquid quench that may also cool and collect a liquid product from a vapour. A recovery unit may also include demisters, fiber filter beds, or other devices used within the art to collect a liquid product from a vapour stream. A recovery unit may comprise one or more components, for example, one or more condensers, which may be linked in series.

In one exemplary embodiment of the invention, sufficient heat is supplied in the thermal extraction system to produce a temperature in the range of from about 250° C. to about 650° C., or any subrange thereof, including, for example, from about 300° C. to about 550° C., or from about 320° C. to about 400° C. A total residence time of the material in the thermal extraction system may be, for example, less than about 30 seconds, for example, in the range of from about 0.1 to about 30 seconds, or any subrange thereof. For instance, in an exemplary embodiment, the total residence time is from about 0.2 to about 5 seconds. In another exemplary embodiment, the total residence time is about 2 seconds, or less. The residence time of the material in the thermal extraction system is measured as the time interval from the heating up of the starting material in the thermal extraction system to quenching (for example, cooling).

Thermal extraction can produce a product stream comprising solid, liquid and/or vapour. The product stream may be fractionated to obtain fractions, which may be collected to obtain one or more extracts. Fractions may be a solid, e.g., a char, a liquid and/or a vapour, or a combination thereof. Fractions or combinations thereof may be obtained comprising a concentrated extract of the desired compound.

Liquid and/or vapour fractions will generally comprise a higher concentration of desired compounds than a solid fraction. However, a solid fraction may also be obtained. For example, during thermal extraction of yew biomass, taxanes may collect and concentrate on the surface, matrices or pores of any solid by-products, such as carbon by-products, which may result in a taxane-rich solid fraction, that can be collected to obtain a taxane-rich extract of the invention.

In one embodiment of the invention, a liquid fraction is obtained by condensing vapours obtained according to the thermal extraction method of the invention. A liquid fraction may also be obtained following removal of solids, such as char, from the liquid and collecting the liquid to obtain an extract according to the invention. A liquid fraction obtained following extraction of plant based biomass material may be, for example, a tar, a pitch, a pyroligneous acid mixture, etc.

In the thermal extraction method of the invention, the liquid and/or vapour fractions may be further fractionated. Each further fraction thus produced may be individually collected to obtain multiple extracts, or collected and combined into one or more extracts. Fractionation may also be used to selectively produce extracts rich in selected compounds, such as selected taxanes.

The extract of the invention (also referred to herein as a "thermal extract") may be the collected solid, liquid or vapour fractions, or any combination thereof. It may also be a fraction of the collected solid, liquid and/or vapour fractions, or a combination of selected collected fractions. A single extract may be obtained by collecting a single fraction or collecting and combining multiple fractions. Multiple extracts may also be obtained by collecting multiple fractions or by collecting multiple combined fractions. Also, the extract may comprise a phase change from the starting material (e.g., solid to liquid, etc.), or not.

It has been observed that thermal extraction can provide higher yields of extracted compounds than yields reported in the literature for other methods, including conventional solvent-recovery extraction and purification methods and other non-solvent methods.

For instance, it has been observed that higher yields of total and specific taxanes, including paclitaxel, may be obtained by thermal extraction. It has further been observed that the taxane-rich extract obtained by thermal extraction has a higher concentration of taxanes in a given volume than in an equivalent volume of *Taxus* or *Austrotaxus* solid biomass starting material or in an equivalent volume of the initial (first-stage) solvent-extract of the *Taxus* or *Austrotaxus* biomass material.

One implication of a more concentrated extract is that, to achieve a comparable amount of finished product, a smaller volume of material is required to be processed in subsequent purification, isolation and recovery steps, than is the case with solid feedstock material or an extract obtained from conventional solvent recovery processes. It has been observed that the initial volume of an enriched extract of the invention to be processed in subsequent purification steps can be lower, for example, an order of magnitude lower, than the volume of initial material required to be processed in a conventional solvent extraction method in order to obtain comparable yields. For instance, for taxanes extraction, thermal extraction may produce a volume of taxane-rich extract that is reduced by factors of, for example, 10, 15, 25 or 50, or greater, or factors in between, when compared to the volume of initial biomass material required to be processed in conventional solvent-extraction methods to obtain comparable yields of purified taxanes.

Taxanes that may be present in a taxane-rich extract of the present invention include one or more than one of the following taxane compounds: paclitaxel, cephalomannine, baccatin III, 10-deacetyltaxol, 10-deacetylcephalomannine, 10-deacetylbaccatin III (also known as 10-DAB or DAB), 13-acetyl-9-dihydrobaccatin III (also known as DHB), 7-xylosyltaxol, 7-xylosylcephalonammine, 7-xylosylbaccatin III, and derivatives and analogs thereof. This listing is not intended to be exhaustive. Other taxanes may also be present in the taxane-rich extract of the present invention.

The fractions produced by thermal extraction, and the taxane-rich extract, may also comprise, in addition to one more taxane compounds, a number of other components, including depolymerized lignin, fragmented cellulose- and hemicellulose-derived products, and other reactive components including phenolics, as well as a number of other components.

It has been observed that thermal extraction gives a higher overall yield of taxanes, and higher yields of taxanes that are of present commercial value, than known methods of taxane recovery or production. The observed "fingerprint" or relative distribution of the predominant taxane components in the extract, and the concentration of taxanes in the extract obtained by thermal extraction is also different than extracts obtained by current methods. For example, it has been observed that paclitaxel yields can be increased by a factor of about 3 to about 5 (i.e., about 300 to about 500%), DHB yields can be increased by a factor of about 2 to about 3 (i.e., about 200 to about 300%), DAB yields increased by a factor of about 8 (i.e., about 800%) and overall taxane yields can be increased by a factor of about 20 (i.e., about 2000%), compared to average yields obtained from solvent extraction of yew needles and clippings, as reported in the literature.

According to one theory of the invention, which is not to be considered limiting on the scope of the invention, thermal extraction is believed to liberate compounds that may be either chemically bound or physically isolated (e.g., in cellular structures) and therefore not as available for recovery by solvent methods. In these cases, the thermal extraction of the present invention, while extracting free and available desired compounds, may simultaneously free and extract bound or isolated compounds by rupturing weak chemical bonds and/or rupturing any physical structures which may isolate or inhibit extraction by conventional means. For instance, where the starting material is a biomass, desired compounds may be contained in vacuoles that can be disrupted by thermal extraction to liberate the whole of the contents, which disruption and liberation would not normally occur by using conventional methods of extraction.

Extracts of the invention, including, but not limited to, liquids, liquid fractions, solids and solid fractions may be further processed by various methods known to those skilled in the art to purify, isolate and recover the desired compounds for commercial use.

For instance, where taxanes are recovered, the method of the present invention may further comprise a step of contacting taxane-rich extracts obtained, including, for example, the whole extract obtained by combining all of the fractions collected, selected liquid fractions collected, and solid carbon fractions collected, with water or some other appropriate partitioning solvent to further separate, isolate and concentrate the taxane components. The addition of water or some other appropriate partitioning solvent may occur directly in the thermal extraction system (i.e., in situ), particularly in product recovery units, during processing of the biomass, or as a separate step, or steps, after the product is recovered from the thermal extraction process.

Furthermore, the thermal extraction method of the present invention may further comprise a step of fractionation for the purpose of isolating and concentrating certain desired compounds fractions from other less desirable components. (For instance, where taxanes are extracted certain desired taxanes could be separated from less desirable taxanes, phenolics, lignocellulosics, inhibitors, and other contaminants.) The removal of non-desirable components may be carried out to simplify subsequent purification steps or to increase the intermediate economic value.

The isolated yield of paclitaxel obtained by current organic solvent extraction techniques from the bark of *Taxus* is typically in the order of 0.01%, and from clipping and needles, about 0.003 to about 0.015%. However, with the methods of the present invention, isolated yields of about 0.031 to 0.049% have been obtained. The isolated yield of DHB from clippings and needles, as obtained by current organic solvent extraction techniques, is typically on the order of 0.04%. However, with the methods of the present invention, isolated DHB yields of between 0.08 and 0.12% have been obtained. The isolated yield of DAB from clippings and needles, as obtained by current organic solvent extraction techniques, is typically on the order of 0.06%. However, with the methods of the present invention, isolated DAB yields of between 0.46 and 0.53% have been obtained. The yield of total taxanes recovered from clippings and needles, as obtained by current organic solvent extraction techniques, is typically on the order of 0.25%. However, with the methods of the present invention, total taxane yields of between 5 and 7% have been measured.

Thermal extraction can also be used on a starting material, which may have been initially processed, including by solvent extraction. It has been observed, for example, that caffeine can be thermally extracted from a fresh source, or following a solvent extraction.

An example of a thermal extraction system suitable for preparing an extract or extracts according to the present invention is described in U.S. Pat. No. 6,844,420 (Freel and Graham); the disclosure of which is incorporated herein by reference, and is diagrammatically presented in FIG. 1. Briefly, the system includes a feed system (10), a contained vessel (20), a particulate inorganic heat carrier reheating system (30), and for the purposes of the invention described herein, at least one recovery unit, which as shown in FIG. 1, and which is not to be considered limiting in any manner, may comprise a primary (40) and a secondary (50) condenser through which the product vapor streams produced during thermal extraction are cooled and collected for example using a liquid quench (80). The recovery unit may also include a demister (60) and a fiber filter bed (70) or other device to collect the liquid product. The thermally extracted product composition of this invention may be derived from a selected product fraction obtained from at least one recovery unit, for example the primary, or the secondary recovery unit, or a combination thereof, or it may be a whole oil (i.e, whole thermal liquid product) obtained from first and second recovery units, including demisters and fiber filter bed, or a combination thereof. However, it is to be understood that analogous thermal extraction systems, comprising different number or size of recovery units, or different condensing means may be used for the selective preparation of the extract for the purpose of the present invention.

The recovery unit system used within the thermal extraction reactor system, outlined in FIG. 1, which is not to be considered limiting in any manner, may involve the use of direct-liquid contact condensers (80) to cool the thermal extraction product. However, it is to be understood that any suitable recovery unit may be used, including surface condensers. In one embodiment, liquid, used within these condensers (80) to cool the thermal extraction product, is obtained from the corresponding cooled primary or secondary condenser product (90). However, as would be evident to one of skill in the art, any other compatible liquid for cooling the product within the primary and secondary recovery units, or a combination thereof, may also be used for this purpose. Furthermore, it is considered within the scope of this invention that other scrubber or cooling means including heat exchangers comprising solid surfaces and the like may also be used for cooling the product vapors.

Examples 1 and 2

A. Description of a Feed Material—Canada Yew

*Taxus Canadensis* Marsh, Canada yew, ground hemlock shrubs were collected in July-September 2004 from Sault Ste. Marie surrounding area, Ontario, Canada (lat. 46.34 N, long. 84.17 W). Pressed voucher specimens are deposited in the Canadian Forest Service-Sault Ste. Marie herbarium as *Taxus canadensis* Marsh (2004—4001-10 CFS-SSM #s), Taxaceae—yew family. The fresh *T. Canadensis* needles and twigs were air dried at room temperature 22-24° C. The dried sample was ground to ~0.5 mm particle size in a Thomas-Wiley Laboratory mill, Model 4 (Thomas Scientific, USA).

B. Analytical Methods and Procedures

Analysis of Taxane Products:

High performance liquid chromatography was performed using a Waters Delta Prep 4000 Liquid Chromatograph equipped with a computer and Empower software, a Waters® 996 autoscan photodiode array spectrophotometric detector; and an analytical column. The analytical column used in the experiments described below was a Curosil-PFP Phenomenox (250×4.60 mm i.d.). A modified gradient chromatographic technique (Phenomenex) was used at room temperature using an acetonitrile/water solvent system. However, other solvent systems were also used. Samples were eluted using an appropriate gradient, for example, a 25/75 to 65/35 gradient of acetonitrile/water over a 40 minute period with a flow rate of 1.0 ml/min. Compounds were detected at a wavelength of 228 nm and resolved peaks were scanned by the photodiode array detector from 200 to 400 nm.

A dilute solution (10 mg/mL) of extract was filtered through 13 mm GHP 0.45 µm Minispike (Waters, EDGE) and 10 µL was injected onto an HPLC column with and without spiking with standards. Peaks were identified on the basis of retention times and UV spectra. Peak heights, measured as absorbance at 228 nm, were converted to mg/ml using conversion factors obtained for commercial taxane standards. Such HPLC analyses were performed in triplicate.

UV spectra were recorded on a UV-Vis. Beckman DU series 640 spectrophotometer. Taxanes were identified by co-chromatography with authentic samples (ChromaDex, Santa Ana, Calif., USA) using TLC and HPLC.

Example 1: Production of Thermal Extract Using Thermal Extraction

A hemlock feedstock, prepared according to the procedure described above, was processed in a thermal extraction system essentially as described in U.S. Pat. No. 6,844,420 (the disclosure of which is incorporated herein by reference). In the thermal extraction system, a char product is rapidly separated from the product vapor/gas stream, and the product vapor and liberated liquids are rapidly quenched within a primary recovery unit using, a direct liquid contact condenser, or a liquid quench, as described below. The compounds remaining within the product vapor are transferred to a secondary recovery unit linked to the primary recovery unit in series. The product vapor is then quenched within the secondary recovery unit using, a direct liquid contact condenser, or a liquid quench, and the condensed product collected. Any remaining product within the product vapor is collected within the demister and filter bed (see FIG. 1). The primary recovery unit product is collected, as well as the secondary recovery unit product. The yield of liquid product from the recovery unit ranges from about 40 to about 60% (w/w), and is typically about 49% (see FIG. 1).

Example 1A: Thermal Extraction Run 1

A hemlock feedstock (4,715 g) containing 2.52 wt % ash and 8.73 wt % moisture was thermally extracted in an upflow reactor (See FIG. 1) at 490° C. using a surface-condenser, to produce a bio-oil sample. The liquid yield on a feed "ash free" basis was 55.49 wt %. Samples of the thermal extract submitted for taxane analysis included an aqueous fraction (1024.5 g), a tar fraction (440.5 g) and pure liquid fraction (170 g) squeezed from a fiberglass filter material in the demister.

Example 1B: Thermal Extraction Run 2

A hemlock feedstock (7,996 g) containing 1.80 wt % ash and 5.20 wt % moisture was thermally extracted in an upflow reactor (See FIG. 1) at 398° C. run in surface-condensing mode, to produce a liquid thermal extract. The liquid yield on a feed "ash free" basis was 45.12 wt %, char was 28.54 wt % and the gas was 17.41 wt %.

Samples of the taxane-containing thermal extract products were taken and submitted for taxane analysis.

In this example, the volume of the thermal extract is reduced by a factor of about 25 (without the requirement for any initial solvent extraction of the solid biomass) when compared to the initial volume of biomass from which the extract was produced.

Figure 2:
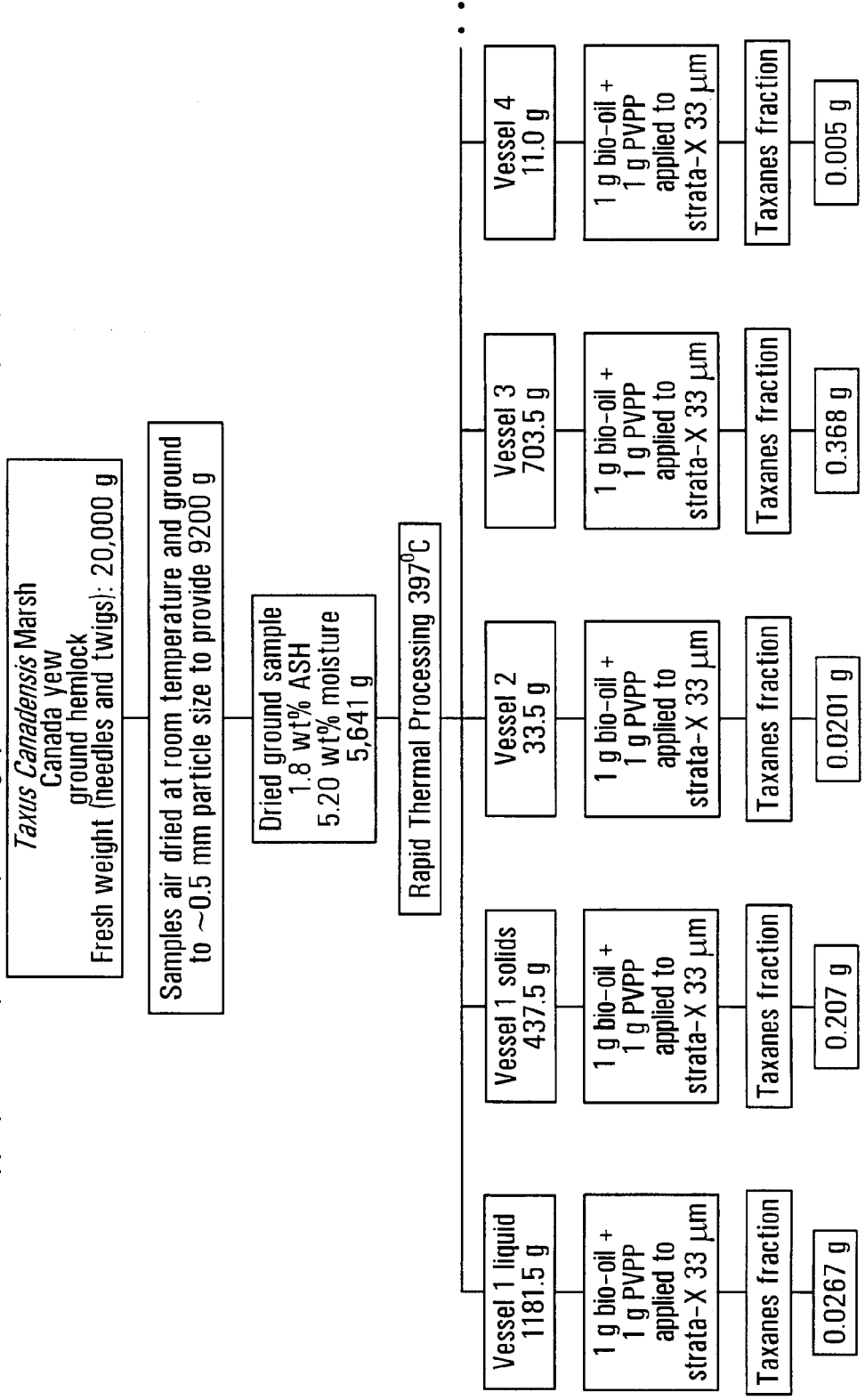
FIG. 2 is a flow chart illustrating a method of the invention according to Example 1C.
Figure 2:
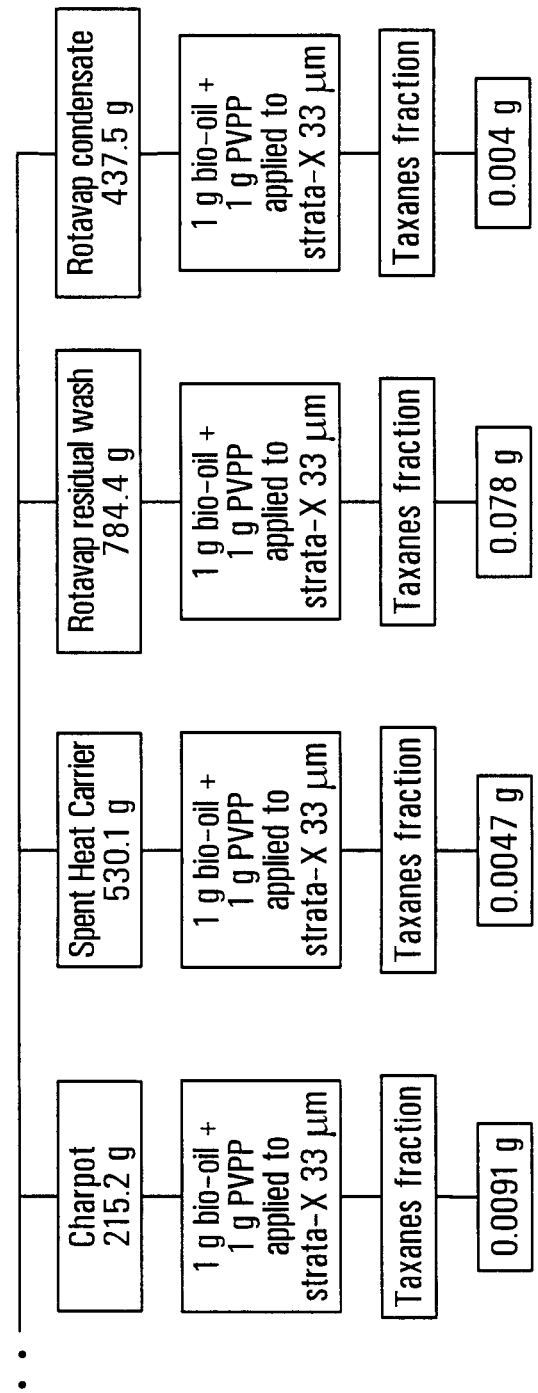

Example 1C: Thermal Extraction Run 3 (See FIG. 2)

A hemlock feedstock (5,641 g) containing 1.80 wt % ash and 5.20 wt % moisture was thermally extracted in an upflow reactor (See FIG. 1) run at 397° C., and in liquid quench mode, to produce liquid thermal extract samples. The quench liquid was an approximate 50/50 mix of the aqueous product from the run of Example 1A, and demineralized water. The liquid yield on a feed "ash free" basis was 46.77 wt %, char was 25.87 wt % and the gas was 19.0 wt %. The purpose of this run was to compare product yields obtained using a liquid quench with that of surface condensing.

Samples of the taxane-containing thermal extraction products were taken and submitted for taxane analysis.

In this example, the volume of the thermal extract is reduced by a factor of about 50 (without the requirement for any initial solvent extraction of the solid biomass) when compared to the initial volume of biomass from which the extract was produced.

Example 1D: Selective Fractionation of Taxanes in the Recovery Train

An example of the selective fractionation and concentration of taxanes in the recovery train is demonstrated in the thermal extraction example described in 1B. In this example, approximately 50% of the identifiable taxane content was detected in the fraction of the thermal extract that was recovered from the fiber bed filter recovery unit, even though this fraction represented only 22% of the total thermal extract produced during Thermal Extraction Run 2.

Example 1E: Further Selective Fractionation of Taxanes in the Recovery Train

An example of further selective fractionation and concentration through the addition of water or other partitioning solvent is demonstrated in the thermal extraction example described in 1C. In this example, water was added in situ in the recovery train, and in the result, approximately 67% of the identifiable taxane content was detected in the fraction of the thermal extract that was recovered from the fiber bed filter recovery unit, even though this fraction represented only 24% of the total thermal extract produced during Thermal Extraction Run 3. Other than the addition of water and direct condensation of the thermal extract products, the thermal extraction conditions of Run 3 were similar to those of Run 2 with respect to temperature and processing time. The selective fractionation of taxanes using water portioning was therefore demonstrated to be more effective in Run 3 when compared to the selective fractionation of taxanes without water partitioning as was the case in Run 2.

Analyses for Examples 1A, 1B and 1C

Thin-layer chromatography (TLC) of the thermal extract using silica gel and methylene chloride:MeOH 95:5 as a solvent was used and proved beneficial in obtaining qualitative analysis of the taxanes (i.e., confirmation of the presence of taxanes in the samples). The results of the TLC analysis are presented in the last column of Table 1 (i.e, taxanes are reported as "detected" or "not detected").

Example 2: Isolation and Quantitative Analyses of Taxanes by Gel Chromatography and HPLC Isolation Method 1:
Thermal extract samples (1 g) obtained as outlined in Examples 1A, 1B and 1C were mixed and adsorbed onto 1 g of Polyvinylpolypyrrolidone, PVPP (Sigma Chemical Co., P-6755 [25249-54-1]) and applied to strata-X 33 μm Polymeric Sorbent 1 g/20 ml Giga Tubes (Phenomenex, 8B-5100-JEG). The strata-X was conditioned with 20 mL methanol and equilibrated with 20 mL D.I. water before loading the above-mentioned sample. Elution was carried out at a slow rate using the following solvent systems:
a) methanol—D.I. water (7:3) [5×12 mL],
b) methanol:acetonitrile:D.I. water (6:3:1), (6:2:2) or (5:2:3) [5×12 mL], and
c) methanol:acetonitrile (1:1) [5×12 mL].
The taxane enriched fractions were analyzed chromatographically by TLC and HPLC. TLC was used for qualitative analysis (Table 1) and HPLC was used for quantitative analysis to determine the yields of total and individual taxanes (Tables 1, 2 and 3). Solvent system "b" (6:3:1) was selected as effective for the quantitative determination of taxane yields, and the yields reported in the Tables were determined using this solvent system.

TABLE 1

TLC and HPLC Analysis

| Sample # | Name | Solvent System | Wt. Of Fraction (g) | % Taxane Yield (HPLC) | TLC Results |
|---|---|---|---|---|---|
| | | Example 1A | | | |
| 1 | 1R104 Aqueous Fraction | A | | | N.D. |
| | | B | 0.0568 | 5.68 | Taxanes fraction |
| | | C | 0.0194 | 1.94 | N.D. |
| 2 | 2R104 Non-Aqueous Fraction | A | | | N.D. |
| | | B | 0.4150 | 41.5 | Taxanes fraction |
| | | C | 0.0325 | 3.25 | N.D. |
| 3 | 3R104 Filter Liquid | A | | | N.D. |
| | | B | 0.4213 | 42.13 | Taxanes fraction |
| | | C | 0.0439 | 4.39 | N.D. |
| | | Example 1B | | | |
| 4 | R129a - Vessel 1 Tar | A | | | N.D. |
| | | B | 0.3738 | 37.38 | Taxanes fraction |
| | | C | 0.0322 | 3.22 | N.D. |

TABLE 1-continued

TLC and HPLC Analysis

| Sample # | Name | Solvent System | Wt. Of Fraction (g) | % Taxane Yield (HPLC) | TLC Results |
|---|---|---|---|---|---|
| 5 | R129a - Recovery Vessel 1 | A | | | N.D. |
| | | B | 0.0234 | 2.34 | N.D. |
| | | C | 0.0013 | 0.13 | N.D. |
| 6 | R129a - Recovery Vessel 2 (demister) | A | | | N.D. |
| | | B | 0.3720 | 37.2 | Taxanes fraction |
| | | C | 0.0310 | 3.1 | N.D. |
| 7 | R129a - Recovery Vessel 3 (filter) | A | | | N.D. |
| | | B | 0.4109 | 41.09 | Taxanes fraction |
| | | C | 0.0337 | 3.37 | N.D. |
| 8 | R129a - Recovery Vessel 4 (bath) | A | | | N.D. |
| | | B | 0.0046 | 0.46 | N.D. |
| | | C | 0.0010 | 0.1 | N.D. |
| 9 | R129a - Rotovap Residual Wash | A | | | N.D. |
| | | B | 0.3158 | 31.58 | Taxanes fraction |
| | | C | 0.0306 | 3.06 | N.D. |
| | Example 1C | | | | |
| 10 | R130a - Recovery Vessel 1 | A | | | N.D. |
| | | B | 0.0267 | 2.67 | Trace |
| | | C | 0.0018 | 0.18 | N.D. |
| 11 | R130a - Solids from Vessel 1 | A | | | N.D. |
| | | B | 0.2079 | 20.79 | Taxanes fraction |
| | | C | 0.0311 | 3.11 | N.D. |
| 12 | R130a - Recovery Vessel 2 (demister) | A | | | N.D. |
| | | B | 0.0201 | 2.01 | Trace |
| | | C | 0.0014 | 0.14 | N.D. |
| 13 | R130a - Vessel 3 (filter) | A | | | N.D. |
| | | B | 0.3682 | 36.82 | Taxanes fraction |
| | | C | 0.0410 | 4.1 | N.D. |
| 14 | R130a - Vessel 4 (bath) | A | | | N.D. |
| | | B | 0.0050 | 0.5 | N.D. |
| | | C | 0.0012 | 0.12 | N.D. |
| 15 | R130a - Rotovapped Residual Wash | A | | | N.D. |
| | | B | 0.0782 | 7.82 | Trace |
| | | C | 0.0021 | 0.21 | N.D. |
| 16 | R130a - Roto-vap Condensate | A | | | N.D. |
| | | B | 0.0041 | 0.41 | N.D. |
| | | C | 0.0014 | 0.14 | N.D. |

Solvent system A. methanol:deionized water (7:3)
Solvent system B. methanol:acetonitrile:D.I. water (6:3:1)
Solvent system C. methanol:acetonitrile (1:1)
N.D. = not detected
Trace = trace amount of taxanes The yield of total taxanes and individual taxane components, as produced via thermal extraction and as recovered using Isolation Method 1, are reported in Tables 2 and 3, respectively. A comparison of total "Isolation Method 1" taxane yields with those reported in the literature for conventional solvent recovery processes (e.g. Daoust, G and Sirois, G., 2003, and "*Canada Yew (Taxus canadensis Marsh.)* and *Taxanes: A Perfect* Species *for Filed Production* and *improvement Through Genetic Selection*" Natural Resources Canada, Canadian Forest Service, Sainte-Foy, Quebec), is also given in Table 2. A comparison of the "Isolation Method 1" yields of individual representative taxanes with the solvent control test yields is also given in Table 3.

As can be observed from the data in Tables 2 and 3, the yields of total taxanes and individual representative taxanes are higher using the methods of the present invention than yields that have been obtained using conventional solvent extraction methods.

TABLE 2

"Isolation Method 1" Yields of Total Taxanes via Thermal Extraction compared with Conventional Solvent Yields (as reported in the literature*)

| RUN# | Extraction Temp. (° C.) | Total Taxane (wt %) |
|---|---|---|
| R-104A | 490 | 5.0 |
| R-129A | 398 | 6.7 |
| R-130A | 397 | 5.2 |
| Solvent Extraction - | | 0.2 |

*Daoust, G and Sirois, G., 2003, "*Canada Yew (Taxus canadensis Marsh.) and Taxanes: A Perfect Species for Filed Production and improvement Through Genetic Selection*" Natural Resources Canada, Canadian Forest Service, Sainte-Foy, Quebec

TABLE 3

"Isolation Method 1" Yields of paclitaxel and Other Taxane Compounds via Thermal Extraction compared with Solvent Extraction (Solvent Control*) Yields

| RUN# | Paclitaxel (wt %) | 10 DAB III (wt %) | Bacatin III (wt %) | Cephalomannine (wt %) | 10-deacetyl-Taxol (wt %) | 7-epi-taxol (wt %) | DHB (wt %) |
|---|---|---|---|---|---|---|---|
| R-104A | 0.031 | 0.49 | 0.29 | 0.61 | 0.39 | 0.37 | 0.092 |
| R-129A | 0.049 | 0.53 | 0.37 | 0.71 | 0.42 | 0.44 | 0.12 |
| R-130A | 0.034 | 0.46 | 0.33 | 0.59 | 0.4 | 0.4 | 0.084 |
| Solvent Control | 0.011 | 0.061 | 0.042 | 0.052 | 0.012 | 0.021 | 0.039 |

*see Example 3

Isolation Method 2:

Liquid thermal extract samples (1 g) obtained as outlined in Examples 1A, 1B and 1C were mixed and adsorbed onto 1 g of Polyvinylpolypyrrolidone, PVPP (Sigma Chemical Co., P-6755 [25249-54-1]) and applied to strata-X 33 µm Polymeric Sorbent 1 g/20 ml Giga Tubes (Phenomenex, 8B-S100-JEG). The strata-X was conditioned with 20 mL methanol and equilibrated with 20 mL D.I. water before loading the above-mentioned sample. Elution was carried out at a slow rate using 20 mL of water followed by 20 mL aliquots of increasing concentrations (20, 50, 70, 100%) of methanol. All fractions were analyzed chromatographically with maximum concentration found in the fraction eluting with 50-70% methanol.

Example 3

Solvent Extraction of Taxanes (Non-Pyrolytic Control Test)

Fresh *Taxus canadensis* Marsh needles (4417.13 g fr. wt.) were extracted at room temperature in two steps: first, by steeping for 24 h in 100% MeOH (1 g fr. wt/10 ml solvent), followed by chopping in a commercial Waring blender and decanting the solvent; second, by steeping the chopped residue for an additional 24 h in 60% aqueous MeOH. The combined methanolic extracts were evaporated under reduced pressure until most or all of the MeOH had been removed. The residue was freeze-dried to obtain 713.88 g of crude extract. Thus from each g fresh weight of needles, 162 mg of *T. canadensis* crude extract was obtained. Results of this test are presented in Table 3 as "solvent control".

Example 4

A post-solvent coffee feedstock was thermally extracted in an upflow reactor (See FIG. 1.) operated at a temperature of 464° C., and in a liquid quench mode, to produce thermal extract samples. The liquid yields on a feed "ash free" basis was 55.15 wt %, the char yield was 16.87 wt %, and the gas yield was 24.37 wt %. The purpose of the run was to determine whether any residual caffeine remaining in post solvent extracted coffee feedstock could be thermally extracted.

A sample of the caffeine-containing thermal extraction products were taken and submitted for caffeine analysis using an Agilent Technologies 1200 Liquid Chromatograph equipped with a computer and Chem. Station software (Chem. 32), a Binary pump SL (G1312B), a high performance autosample SL (G1367C) and an autoscan photo-diode array spectrophotometer detector Agilent Technologies (G1315C).

Results:
R158A Demister Glycol: 91.2 ppm caffeine in 1 g of the oil
R158A Primary Condenser 129 ppm caffeine in 1 g of the oil

Example 5

A flax shive feedstock was thermally extracted in an upflow reactor (See FIG. 1.) operated at a temperature of 500° C., and in a liquid quench mode, to produce thermal extract samples. The liquid yields on a feed "ash free" basis was 55.57 wt %, the char yield was 14.48 wt %, and the gas yield was 23.61 wt %. The purpose of the run was to determine whether any epicatechin and catechin in flax shives could be thermally extracted.

Samples of the collected liquid thermal extract products were taken and submitted for epicatechin and catechin analysis using an Agilent Technologies Eclipse Plus C-18 5 µm (4.6×150 mm i.d.) reverse-phase analytical column. A gradient chromatographic technique was used at room temp: solvent A=MeOH/Acetonitrile (95:5); solvent B=0.05% aq. HCOOH; with the flow rate set at 0.9 ml/min. Three fixed detection wavelengths were used: 270 nm, 280 nm and 350 nm and resolved peaks were scanned by the photodiode array detector from 250 to 400 nm.

Results:
Epicatechin and cathechin were detected in significant quantities

Although the foregoing invention has been described in some detail by way of illustration and example, and with regard to one or more embodiments, for purposes of clarity of understanding, it is readily apparent to those of ordinary skill in the art in light of the teachings of this invention that certain changes, variations and modifications may be made thereto without departing from the spirit or scope of the invention as described in the appended claims.

It must be noted that as used in the specification and the appended claims, the singular forms of "a", "an" and "the" include plural reference unless the context clearly indicates otherwise.

Unless defined otherwise all technical and scientific terms used herein have the same meaning as commonly understood to one of ordinary skill in the art to which this invention belongs.

All publications, patents and patent applications cited in this specification are incorporated herein by reference as if each individual publication, patent or patent application were specifically and individually indicated to be incorporated by reference. The citation of any publication, patent or patent application in this specification is not an admission that the publication, patent or patent application is prior art.

The invention claimed is:

1. A thermal extraction method, comprising:
   i) preparing a diterpenoid-containing biomass starting material comprising a species of the genus *Taxus* or *Austrotaxus*, wherein the biomass is reduced in size to an average diameter of less than about 2 cm in its smallest dimension;
   ii) introducing the reduced size biomass starting material into a thermal extraction system comprising a contained vessel, a heat source, and at least one recovery unit;
   iii) heating the reduced size biomass starting material in the thermal extraction system to a temperature of from about 250° C. to about 650° C. for a residence time of less than about 30 seconds; and
   iv) collecting a condensed thermal extract comprising:
      a) paclitaxel; and
      b) 13-acetyl-9-dihydrobaccatin III, said 13-acetyl-9-dihydrobaccatin III present in an amount that is approximately 10 times greater than the amount of paclitaxel,
   wherein the thermal extraction method is exclusive of a solvent extraction.

2. The thermal extraction method of claim 1, wherein said heating is sufficient to extract non-degraded 13-acetyl-9-dihydrobaccatin III.

3. The thermal extraction method of claim 1, wherein the 13-acetyl-9-dihydrobaccatin III is concentrated 10-fold or more in the thermal extract relative to the starting biomass material.

4. The thermal extraction method of claim 1, wherein said heating is sufficient to extract non-degraded paclitaxel.

5. The method of claim 1, wherein said heating is to a temperature of from about 300° C. to about 550° C. for a residence time of less than about 2 seconds.

6. The method of claim 1, wherein the at least one recovery unit comprises a device to collect the condensed thermal extract, and wherein the device is selected from the group consisting of a condenser, a demister, a fiber bed filter, and combinations thereof.

7. The thermal extraction method of claim 1, wherein collecting the thermal extract comprises collecting a condensed vapor fraction and a liquid fraction.

8. The method of claim 1, further comprising: treating the thermal extract with a partitioning solvent to selectively remove one or more taxanes.

9. The method of claim 1, wherein the thermal extract further comprises: 7-epi-taxol, said 7-epi-taxol present in an amount that is approximately 10 times greater than the amount of paclitaxel.

10. A thermal extraction method, comprising:
    i) preparing a diterpenoid-containing biomass starting material comprising a species of the genus *Taxus* or *Austrotaxus*, wherein the biomass is reduced in size to an average diameter of less than about 2 cm in its smallest dimension;
    ii) introducing the reduced size biomass starting material into a thermal extraction system comprising a contained vessel, a heat source, and at least one recovery unit;
    iii) heating the reduced size biomass starting material in the thermal extraction system to a temperature of from about 250° C. to about 650° C. for a residence time of less than about 30 seconds; and
    iv) collecting a thermal extract comprising:
       a) paclitaxel; and
       b) 7-epi-taxol, said 7-epi-taxol present in an amount that is approximately 10 times greater than the amount of paclitaxel,
    wherein the thermal extraction method is exclusive of a solvent extraction.

11. The thermal extraction method of claim 10, wherein said heating is sufficient to extract non-degraded 7-epi-taxol.

12. The thermal extraction method of claim 10, wherein the 7-epi-taxol is concentrated 10-fold or more in the thermal extract relative to the starting biomass material.

13. The thermal extraction method of claim 10, wherein said heating is sufficient to extract non-degraded paclitaxel.

14. The method of claim 10, wherein said heating is to a temperature of from about 300° C. to about 550° C. for a residence time of less than about 2 seconds.

15. The method of claim 10, wherein the at least one recovery unit comprises a device to collect a liquid fraction from the vapor fraction, and wherein the device is selected from the group consisting of a condenser, a demister, a fiber bed filter, and combinations thereof.

16. The thermal extraction method of claim 10, wherein collecting the thermal extract comprises collecting a condensed vapor fraction and a liquid fraction.

17. The method of claim 10, further comprising: treating the thermal extract with a partitioning solvent to selectively remove one or more taxanes.

* * * * *